(12) United States Patent
Wondka et al.

(10) Patent No.: US 10,099,028 B2
(45) Date of Patent: Oct. 16, 2018

(54) METHODS, SYSTEMS AND DEVICES USING LOX TO PROVIDE VENTILATORY SUPPORT

(75) Inventors: Anthony D. Wondka, Thousand Oaks, CA (US); Joseph Cipollone, Laguna Niguel, CA (US); Todd W. Allum, Livermore, CA (US)

(73) Assignee: Breathe Technologies, Inc., Irvine, CA (US)

( * ) Notice: Subject to any disclaimer, the term of this patent is extended or adjusted under 35 U.S.C. 154(b) by 1230 days.

(21) Appl. No.: 13/211,248

(22) Filed: Aug. 16, 2011

(65) Prior Publication Data

US 2012/0118285 A1 May 17, 2012

Related U.S. Application Data

(60) Provisional application No. 61/374,126, filed on Aug. 16, 2010.

(51) Int. Cl.
*A61M 16/10* (2006.01)
*A61M 16/12* (2006.01)
(Continued)

(52) U.S. Cl.
CPC ........ *A61M 16/10* (2013.01); *A61M 16/0677* (2014.02); *A61M 16/109* (2014.02); *A61M 16/125* (2014.02); *F17C 7/04* (2013.01); *A61M 15/00* (2013.01); *A61M 16/0096* (2013.01); *A61M 2016/0024* (2013.01); *A61M 2202/025* (2013.01); *A61M 2202/0208* (2013.01);
(Continued)

(58) Field of Classification Search
CPC .. A61M 16/10; A61M 16/1005; A61M 16/18; F17C 7/00; F17C 7/02; F17C 7/04; F02G 1/043; F25B 9/14
See application file for complete search history.

(56) References Cited

U.S. PATENT DOCUMENTS

| 50,641 A | 10/1865 | Stone |
| 428,592 A | 5/1890 | Chapman |

(Continued)

FOREIGN PATENT DOCUMENTS

| DE | 19626924 | 1/1998 |
| DE | 29902267 U1 | 7/1999 |

(Continued)

OTHER PUBLICATIONS

In the U.S. Patent and Trademark Office, Supplemental Notice of Allowance dated in re: U.S. Appl. No. 10/771,803, dated Dec. 2, 2008, 2 pages.

(Continued)

*Primary Examiner* — Kathryn E Ditmer
(74) *Attorney, Agent, or Firm* — Stetina Brunda Garred and Brucker; Mark B. Garred

(57) ABSTRACT

A portable liquid oxygen system may provide an average flow rate of oxygen gas at approximately 6-approximately 20 lpm using a rapid gas conversion mode. The rapid gas conversion mode utilizes a Stirling engine that harnesses the heat differential between the ambient temperature and the liquid oxygen store to drive a fan. The fan operates to blow ambient air across a heat exchanger, which allows the heat exchanger to more rapidly evaporate liquid oxygen into oxygen gas.

19 Claims, 9 Drawing Sheets

(51) Int. Cl.
*F17C 7/04* (2006.01)
*A61M 16/06* (2006.01)
*A61M 15/00* (2006.01)
*A61M 16/00* (2006.01)

(52) U.S. Cl.
CPC .......... *A61M 2202/0275* (2013.01); *A61M 2230/205* (2013.01); *A61M 2230/60* (2013.01); *A61M 2230/63* (2013.01); *F17C 2201/058* (2013.01); *F17C 2205/0335* (2013.01); *F17C 2205/0338* (2013.01); *F17C 2221/011* (2013.01); *F17C 2223/0161* (2013.01); *F17C 2223/033* (2013.01); *F17C 2225/0123* (2013.01); *F17C 2227/0304* (2013.01); *F17C 2227/0313* (2013.01); *F17C 2250/03* (2013.01); *F17C 2250/043* (2013.01); *F17C 2250/0443* (2013.01); *F17C 2250/0621* (2013.01); *F17C 2250/0626* (2013.01); *F17C 2250/0636* (2013.01); *F17C 2270/025* (2013.01)

(56) References Cited

U.S. PATENT DOCUMENTS

| | | | |
|---|---|---|---|
| 697,181 | A | 4/1902 | Smith |
| 718,785 | A | 1/1903 | McNary |
| 853,439 | A | 5/1907 | Clark |
| 859,156 | A | 7/1907 | Warnken |
| 909,002 | A | 1/1909 | Lambert |
| 1,125,542 | A | 1/1915 | Humphries |
| 1,129,619 | A | 2/1915 | Zapf |
| 1,331,297 | A | 2/1920 | Walker |
| 2,119,494 | A * | 5/1938 | Smith ............... F25B 15/10 62/238.3 |
| 2,178,800 | A | 11/1939 | Lombard |
| 2,259,817 | A | 10/1941 | Hawkins |
| 2,552,595 | A | 5/1951 | Seeler |
| 2,663,297 | A | 12/1953 | Turnberg |
| 2,693,800 | A | 11/1954 | Caldwell |
| 2,735,432 | A | 2/1956 | Hudson |
| 2,792,000 | A | 5/1957 | Richardson |
| 2,843,122 | A | 7/1958 | Hudson |
| 2,859,748 | A | 11/1958 | Hudson |
| 2,931,358 | A | 4/1960 | Sheridan |
| 2,947,938 | A | 8/1960 | Bennett |
| 3,172,407 | A | 3/1965 | Von Pechmann |
| 3,267,935 | A | 8/1966 | Andreasen et al. |
| 3,319,627 | A | 5/1967 | Windsor |
| 3,357,424 | A | 12/1967 | Schreiber |
| 3,357,427 | A | 12/1967 | Wittke et al. |
| 3,357,428 | A | 12/1967 | Carlson |
| 3,435,623 | A * | 4/1969 | Tyree, Jr. ............ F17C 9/02 62/50.2 |
| 3,437,274 | A | 4/1969 | Apri |
| 3,460,533 | A | 8/1969 | Riú Plá |
| 3,479,832 | A * | 11/1969 | Sarsten et al. ............ 62/50.3 |
| 3,493,703 | A | 2/1970 | Finan |
| 3,513,844 | A | 5/1970 | Smith |
| 3,610,247 | A | 10/1971 | Jackson |
| 3,625,206 | A | 12/1971 | Charnley |
| 3,625,207 | A | 12/1971 | Agnew |
| 3,631,438 | A | 12/1971 | Lewin |
| 3,643,660 | A | 2/1972 | Hudson et al. |
| 3,657,740 | A | 4/1972 | Cialone |
| 3,682,171 | A | 8/1972 | Dali et al. |
| 3,721,233 | A | 3/1973 | Montgomery et al. |
| 3,726,275 | A | 4/1973 | Jackson et al. |
| 3,727,606 | A | 4/1973 | Sielaff |
| 3,733,008 | A | 5/1973 | Churchill et al. |
| 3,741,208 | A | 6/1973 | Jonsson et al. |
| 3,754,552 | A | 8/1973 | King |
| 3,794,026 | A | 2/1974 | Jacobs |
| 3,794,072 | A | 2/1974 | Diedrich et al. |
| 3,802,431 | A | 4/1974 | Farr |
| 3,831,596 | A | 8/1974 | Cavallo |
| 3,881,480 | A | 5/1975 | Lafourcade |
| 3,896,800 | A | 7/1975 | Cibulka |
| 3,903,881 | A | 9/1975 | Weigl |
| 3,905,362 | A | 9/1975 | Eyrick et al. |
| 3,949,749 | A | 4/1976 | Stewart |
| 3,951,143 | A | 4/1976 | Kitrilakis et al. |
| 3,961,627 | A | 6/1976 | Ernst et al. |
| 3,972,327 | A | 8/1976 | Ernst et al. |
| 3,985,131 | A | 10/1976 | Buck et al. |
| 3,991,790 | A | 11/1976 | Russell |
| 4,003,377 | A | 1/1977 | Dahl |
| 4,036,253 | A | 7/1977 | Fegan et al. |
| 4,054,133 | A | 10/1977 | Myers |
| 4,067,328 | A | 1/1978 | Manley |
| 4,106,505 | A | 8/1978 | Salter et al. |
| 4,146,885 | A | 3/1979 | Lawson, Jr. |
| 4,206,754 | A | 6/1980 | Cox et al. |
| 4,211,086 | A | 7/1980 | Leonard et al. |
| 4,216,769 | A | 8/1980 | Grimes |
| 4,227,374 | A * | 10/1980 | Oxley ............... 60/651 |
| 4,231,363 | A | 11/1980 | Grimes |
| 4,231,365 | A | 11/1980 | Scarberry |
| 4,256,101 | A | 3/1981 | Ellestad |
| 4,261,355 | A | 4/1981 | Glazener |
| 4,263,908 | A | 4/1981 | Mizerak |
| 4,265,237 | A | 5/1981 | Schwanbom et al. |
| 4,266,540 | A | 5/1981 | Panzik et al. |
| 4,273,124 | A | 6/1981 | Zimmerman |
| 4,274,162 | A | 6/1981 | Joy et al. |
| 4,278,082 | A | 7/1981 | Blackmer |
| 4,282,869 | A | 8/1981 | Zidulka |
| 4,306,567 | A | 12/1981 | Krasner |
| 4,323,064 | A | 4/1982 | Hoenig et al. |
| 4,354,488 | A | 10/1982 | Bartos |
| 4,365,636 | A | 12/1982 | Barker |
| 4,367,735 | A | 1/1983 | Dali |
| 4,377,162 | A | 3/1983 | Stayer |
| 4,393,869 | A | 7/1983 | Boyarsky et al. |
| 4,406,283 | A | 9/1983 | Bir |
| 4,411,267 | A | 10/1983 | Heyman |
| 4,413,514 | A | 11/1983 | Bowman |
| 4,421,113 | A | 12/1983 | Gedeon et al. |
| 4,422,456 | A | 12/1983 | Tiep |
| 4,449,523 | A | 5/1984 | Szachowicz et al. |
| 4,454,880 | A | 6/1984 | Muto et al. |
| 4,462,398 | A | 7/1984 | Durkan et al. |
| 4,469,097 | A | 9/1984 | Kelman |
| 4,481,944 | A | 11/1984 | Bunnell |
| 4,487,256 | A * | 12/1984 | Lutjens ............... F28F 1/20 165/183 |
| 4,488,548 | A | 12/1984 | Agdanowski |
| 4,495,946 | A | 1/1985 | Lemer |
| 4,506,666 | A | 3/1985 | Durkan |
| 4,506,667 | A | 3/1985 | Ansite |
| 4,514,979 | A * | 5/1985 | Mohr ............... F02G 1/02 60/512 |
| 4,519,387 | A | 5/1985 | Durkan et al. |
| 4,520,812 | A | 6/1985 | Freitag et al. |
| 4,527,557 | A | 7/1985 | DeVries et al. |
| 4,535,766 | A | 8/1985 | Baum |
| 4,537,188 | A | 8/1985 | Phuc |
| 4,539,984 | A | 9/1985 | Kiszel et al. |
| 4,548,590 | A | 10/1985 | Green |
| 4,559,940 | A | 12/1985 | McGinnis |
| 4,570,631 | A | 2/1986 | Durkan |
| 4,571,741 | A | 2/1986 | Guillaumot |
| 4,584,996 | A | 4/1986 | Blum |
| 4,590,951 | A | 5/1986 | O'Connor |
| 4,592,349 | A | 6/1986 | Bird |
| 4,621,632 | A | 11/1986 | Bartels et al. |
| 4,630,606 | A | 12/1986 | Weerda et al. |
| 4,630,614 | A | 12/1986 | Atlas |
| 4,644,947 | A | 2/1987 | Whitwam et al. |
| 4,648,395 | A | 3/1987 | Sato et al. |
| 4,648,398 | A | 3/1987 | Agdanowski et al. |
| 4,658,832 | A | 4/1987 | Brugnoli |
| 4,660,555 | A | 4/1987 | Payton |

(56) References Cited

U.S. PATENT DOCUMENTS

| | | |
|---|---|---|
| 4,682,591 A | 7/1987 | Jones |
| 4,684,398 A | 8/1987 | Dunbar et al. |
| 4,686,974 A | 8/1987 | Sato et al. |
| 4,686,975 A | 8/1987 | Naimon et al. |
| 4,688,961 A | 8/1987 | Shioda et al. |
| 4,705,034 A | 11/1987 | Perkins |
| 4,744,356 A | 5/1988 | Greenwood |
| 4,747,403 A | 5/1988 | Gluck et al. |
| 4,753,233 A | 6/1988 | Grimes |
| 4,773,411 A | 9/1988 | Downs |
| 4,776,333 A | 10/1988 | Miyamae |
| 4,782,832 A | 11/1988 | Trimble et al. |
| 4,784,130 A | 11/1988 | Kenyon et al. |
| 4,803,981 A | 2/1989 | Vickery |
| 4,807,616 A | 2/1989 | Adahan |
| 4,807,617 A | 2/1989 | Nesti |
| 4,808,160 A | 2/1989 | Timmons et al. |
| 4,813,431 A | 3/1989 | Brown |
| 4,817,897 A | 4/1989 | Kreusel |
| 4,818,320 A | 4/1989 | Weichselbaum |
| 4,823,788 A | 4/1989 | Smith et al. |
| 4,825,859 A | 5/1989 | Lambert |
| 4,827,922 A | 5/1989 | Champain et al. |
| 4,832,014 A | 5/1989 | Perkins |
| 4,838,255 A | 6/1989 | Lambert |
| 4,841,953 A | 6/1989 | Dodrill |
| 4,848,333 A | 7/1989 | Waite |
| 4,850,350 A | 7/1989 | Jackson |
| 4,865,586 A | 9/1989 | Hedberg |
| 4,869,718 A | 9/1989 | Brader |
| 4,899,740 A | 2/1990 | Napolitano |
| 4,905,688 A | 3/1990 | Vicenzi et al. |
| 4,915,103 A | 4/1990 | Visveshwara et al. |
| 4,915,105 A | 4/1990 | Lee |
| 4,919,128 A | 4/1990 | Kopala et al. |
| 4,919,132 A | 4/1990 | Miser |
| 4,938,212 A | 7/1990 | Snook et al. |
| 4,944,310 A | 7/1990 | Sullivan |
| 4,967,743 A | 11/1990 | Lambert |
| 4,971,049 A | 11/1990 | Rotariu et al. |
| 4,982,735 A | 1/1991 | Yagata et al. |
| 4,986,269 A | 1/1991 | Hakkinen |
| 4,989,599 A | 2/1991 | Carter |
| 4,990,157 A | 2/1991 | Roberts et al. |
| 5,000,175 A | 3/1991 | Pue |
| 5,002,050 A | 3/1991 | McGinnis |
| 5,005,570 A | 4/1991 | Perkins |
| 5,018,519 A | 5/1991 | Brown |
| 5,022,394 A | 6/1991 | Chmielinski |
| 5,024,219 A | 6/1991 | Dietz |
| 5,025,805 A | 6/1991 | Nutter |
| 5,038,771 A | 8/1991 | Dietz |
| 5,042,478 A | 8/1991 | Kopala et al. |
| 5,046,491 A | 9/1991 | Derrick |
| 5,046,492 A | 9/1991 | Stackhouse et al. |
| 5,048,515 A | 9/1991 | Sanso |
| 5,048,516 A | 9/1991 | Soderberg |
| 5,052,400 A | 10/1991 | Dietz |
| 5,054,484 A | 10/1991 | Hebeler, Jr. |
| 5,058,580 A | 10/1991 | Hazard |
| 5,074,299 A | 12/1991 | Dietz |
| 5,076,267 A | 12/1991 | Pasternack |
| 5,090,408 A | 2/1992 | Spofford et al. |
| 5,097,827 A | 3/1992 | Izumi |
| 5,099,836 A | 3/1992 | Rowland et al. |
| 5,099,837 A | 3/1992 | Russel, Sr. et al. |
| 5,101,820 A | 4/1992 | Christopher |
| 5,103,815 A | 4/1992 | Siegel et al. |
| 5,105,807 A | 4/1992 | Kahn et al. |
| 5,107,830 A | 4/1992 | Younes |
| 5,107,831 A | 4/1992 | Halpern et al. |
| 5,113,857 A | 5/1992 | Dickerman et al. |
| 5,117,818 A | 6/1992 | Palfy |
| 5,117,819 A | 6/1992 | Servidio et al. |
| 5,127,400 A | 7/1992 | DeVries et al. |
| 5,134,995 A | 8/1992 | Gruenke et al. |
| 5,134,996 A | 8/1992 | Bell |
| 5,140,045 A | 8/1992 | Askanazi et al. |
| 5,148,802 A | 9/1992 | Sanders et al. |
| 5,161,525 A | 11/1992 | Kimm et al. |
| 5,165,397 A | 11/1992 | Arp |
| 5,181,509 A | 1/1993 | Spofford et al. |
| 5,184,610 A | 2/1993 | Marten et al. |
| 5,186,167 A | 2/1993 | Kolobow |
| 5,193,532 A | 3/1993 | Moa et al. |
| 5,193,533 A | 3/1993 | Body et al. |
| 5,199,424 A | 4/1993 | Sullivan et al. |
| 5,211,170 A | 5/1993 | Press |
| 5,217,008 A | 6/1993 | Lindholm |
| 5,233,978 A | 8/1993 | Callaway |
| 5,233,979 A | 8/1993 | Strickland |
| 5,239,994 A | 8/1993 | Atkins |
| 5,239,995 A | 8/1993 | Estes et al. |
| 5,243,972 A | 9/1993 | Huang |
| 5,245,995 A | 9/1993 | Sullivan et al. |
| 5,255,675 A | 10/1993 | Kolobow |
| 5,258,027 A | 11/1993 | Berghaus |
| 5,269,296 A | 12/1993 | Landis |
| 5,271,388 A | 12/1993 | Whitwam et al. |
| 5,271,391 A | 12/1993 | Graves |
| 5,275,159 A | 1/1994 | Griebel |
| 5,279,288 A | 1/1994 | Christopher |
| 5,287,852 A | 2/1994 | Arkinstall |
| 5,303,698 A | 4/1994 | Tobia et al. |
| 5,303,700 A | 4/1994 | Weismann et al. |
| 5,318,019 A | 6/1994 | Celaya |
| 5,320,167 A * | 6/1994 | Johnson ............... B60H 1/3202 165/61 |
| 5,331,995 A | 7/1994 | Westfall et al. |
| 5,335,656 A | 8/1994 | Bowe et al. |
| 5,339,809 A | 8/1994 | Beck, Jr. et al. |
| 5,349,946 A | 9/1994 | McComb |
| 5,368,017 A | 11/1994 | Sorenson et al. |
| 5,370,112 A | 12/1994 | Perkins |
| 5,373,842 A | 12/1994 | Olsson et al. |
| 5,375,593 A | 12/1994 | Press |
| 5,388,575 A | 2/1995 | Taube |
| 5,394,870 A | 3/1995 | Johansson |
| 5,398,676 A | 3/1995 | Press et al. |
| 5,398,682 A | 3/1995 | Lynn |
| 5,400,778 A | 3/1995 | Jonson et al. |
| 5,419,314 A | 5/1995 | Christopher |
| 5,438,979 A | 8/1995 | Johnson, Jr. et al. |
| 5,438,980 A | 8/1995 | Phillips |
| 5,443,075 A | 8/1995 | Holscher |
| 5,460,174 A | 10/1995 | Chang |
| 5,460,613 A | 10/1995 | Ulrich et al. |
| 5,474,062 A | 12/1995 | DeVries et al. |
| 5,477,852 A | 12/1995 | Landis et al. |
| 5,485,850 A | 1/1996 | Dietz |
| 5,490,502 A | 2/1996 | Rapoport et al. |
| 5,503,146 A | 4/1996 | Froehlich et al. |
| 5,503,497 A | 4/1996 | Dudley et al. |
| 5,507,282 A | 4/1996 | Younes |
| 5,509,409 A | 4/1996 | Weatherholt |
| 5,513,628 A | 5/1996 | Coles et al. |
| 5,513,631 A | 5/1996 | McWilliams |
| 5,513,635 A | 5/1996 | Bedi |
| 5,522,382 A | 6/1996 | Sullivan et al. |
| 5,526,806 A | 6/1996 | Sansoni |
| 5,529,060 A | 6/1996 | Salmon et al. |
| 5,533,506 A | 7/1996 | Wood |
| 5,535,738 A | 7/1996 | Estes et al. |
| 5,537,997 A | 7/1996 | Mechlenburg et al. |
| 5,538,002 A | 7/1996 | Boussignac et al. |
| 5,542,415 A | 8/1996 | Brody |
| 5,546,935 A | 8/1996 | Champeau |
| 5,549,106 A | 8/1996 | Gruenke et al. |
| 5,551,419 A | 9/1996 | Froehlich et al. |
| 5,558,086 A | 9/1996 | Smith et al. |
| 5,564,416 A | 10/1996 | Jones |
| 5,575,282 A | 11/1996 | Knoch et al. |
| 5,582,164 A | 12/1996 | Sanders |
| 5,593,143 A | 1/1997 | Ferrarin |

(56) References Cited

U.S. PATENT DOCUMENTS

| | | |
|---|---|---|
| 5,595,174 A | 1/1997 | Gwaltney |
| 5,598,837 A | 2/1997 | Sirianne, Jr. et al. |
| 5,598,840 A | 2/1997 | Iund et al. |
| 5,603,315 A | 2/1997 | Sasso, Jr. |
| 5,605,148 A | 2/1997 | Jones |
| 5,626,131 A | 5/1997 | Chua et al. |
| 5,632,269 A | 5/1997 | Zdrojkowski |
| 5,636,630 A | 6/1997 | Miller et al. |
| 5,645,053 A | 7/1997 | Remmers et al. |
| 5,645,054 A | 7/1997 | Cotner et al. |
| 5,647,351 A | 7/1997 | Weismann et al. |
| 5,669,377 A | 9/1997 | Fenn |
| 5,669,380 A | 9/1997 | Garry et al. |
| 5,676,132 A | 10/1997 | Tillotson et al. |
| 5,676,135 A | 10/1997 | McClean |
| 5,682,878 A | 11/1997 | Ogden |
| 5,682,881 A | 11/1997 | Winthrop et al. |
| 5,687,713 A | 11/1997 | Bahr et al. |
| 5,687,714 A | 11/1997 | Kolobow et al. |
| 5,687,715 A | 11/1997 | Landis et al. |
| 5,690,097 A | 11/1997 | Howard et al. |
| 5,692,497 A | 12/1997 | Schnitzer et al. |
| 5,697,364 A | 12/1997 | Chua et al. |
| 5,704,345 A | 1/1998 | Berthon-Jones |
| 5,711,296 A | 1/1998 | Kolobow |
| 5,715,812 A | 2/1998 | Deighan et al. |
| 5,715,815 A | 2/1998 | Lorenzen et al. |
| 5,720,278 A | 2/1998 | Lachmann et al. |
| 5,735,268 A | 4/1998 | Chua et al. |
| 5,735,272 A | 4/1998 | Dillon et al. |
| 5,740,796 A | 4/1998 | Skog |
| 5,752,511 A | 5/1998 | Simmons et al. |
| 5,762,638 A | 6/1998 | Shikani et al. |
| 5,791,337 A | 8/1998 | Coles et al. |
| 5,819,723 A | 10/1998 | Joseph |
| 5,826,579 A | 10/1998 | Remmers et al. |
| 5,845,636 A | 12/1998 | Gruenke et al. |
| 5,865,173 A | 2/1999 | Froehlich |
| 5,865,174 A | 2/1999 | Kloeppel |
| 5,881,723 A | 3/1999 | Wallace et al. |
| 5,904,648 A | 5/1999 | Arndt et al. |
| 5,906,204 A | 5/1999 | Beran et al. |
| 5,911,756 A | 6/1999 | Debry |
| 5,915,379 A | 6/1999 | Wallace et al. |
| 5,915,381 A | 6/1999 | Nord |
| 5,918,597 A | 7/1999 | Jones et al. |
| 5,921,238 A | 7/1999 | Bourdon |
| 5,921,942 A | 7/1999 | Remmers et al. |
| 5,921,952 A | 7/1999 | Desmond, III et al. |
| 5,927,276 A | 7/1999 | Rodriguez |
| 5,927,400 A | 7/1999 | Bononi et al. |
| 5,928,189 A | 7/1999 | Phillips et al. |
| 5,931,160 A | 8/1999 | Gilmore et al. |
| 5,931,162 A | 8/1999 | Christian |
| 5,937,853 A | 8/1999 | Strom |
| 5,937,855 A | 8/1999 | Zdrojkowski et al. |
| 5,938,118 A | 8/1999 | Cooper |
| 5,954,050 A | 9/1999 | Christopher |
| 5,957,136 A | 9/1999 | Magidson et al. |
| 5,964,223 A | 10/1999 | Baran |
| 5,975,077 A | 11/1999 | Hofstetter et al. |
| 5,975,081 A | 11/1999 | Hood et al. |
| 5,979,440 A | 11/1999 | Honkonen et al. |
| 5,989,193 A | 11/1999 | Sullivan |
| 6,000,396 A | 12/1999 | Melker et al. |
| 6,019,101 A | 2/2000 | Cotner et al. |
| 6,039,696 A | 3/2000 | Bell |
| 6,050,260 A | 4/2000 | Daniell et al. |
| 6,076,519 A | 6/2000 | Johnson |
| 6,085,747 A | 7/2000 | Axe et al. |
| 6,091,973 A | 7/2000 | Colla et al. |
| 6,093,169 A | 7/2000 | Cardoso |
| 6,095,505 A | 8/2000 | Miller |
| 6,105,575 A | 8/2000 | Estes et al. |
| 6,109,264 A | 8/2000 | Sauer |
| 6,112,746 A | 9/2000 | Kwok et al. |
| 6,119,694 A | 9/2000 | Correa et al. |
| 6,120,460 A | 9/2000 | Abreu |
| 6,123,668 A | 9/2000 | Abreu |
| 6,131,571 A | 10/2000 | Lampotang et al. |
| 6,135,970 A | 10/2000 | Kadhiresan et al. |
| 6,152,132 A | 11/2000 | Psaros |
| 6,152,134 A | 11/2000 | Webber et al. |
| 6,158,432 A | 12/2000 | Biondi et al. |
| 6,192,883 B1 | 2/2001 | Miller, Jr. |
| 6,203,502 B1 | 3/2001 | Hilgendorf et al. |
| 6,213,119 B1 | 4/2001 | Brydon et al. |
| 6,213,955 B1 | 4/2001 | Karakasoglu et al. |
| 6,220,244 B1 | 4/2001 | McLaughlin |
| 6,224,560 B1 | 5/2001 | Gazula et al. |
| 6,227,200 B1 | 5/2001 | Crump et al. |
| 6,247,470 B1 | 6/2001 | Ketchedjian |
| 6,269,811 B1 | 8/2001 | Duff et al. |
| 6,269,812 B1 | 8/2001 | Wallace et al. |
| 6,273,859 B1 | 8/2001 | Remmers et al. |
| 6,286,508 B1 | 9/2001 | Remmers et al. |
| D449,376 S | 10/2001 | McDonald et al. |
| D449,883 S | 10/2001 | McDonald et al. |
| 6,298,850 B1 | 10/2001 | Argraves |
| 6,305,374 B1 | 10/2001 | Zdrojkowski et al. |
| 6,314,957 B1 | 11/2001 | Boissin et al. |
| 6,315,739 B1 | 11/2001 | Merilainen et al. |
| D451,598 S | 12/2001 | McDonald et al. |
| 6,328,038 B1 | 12/2001 | Kessler et al. |
| 6,328,753 B1 | 12/2001 | Zammit |
| 6,332,463 B1 | 12/2001 | Farrugia et al. |
| 6,345,619 B1 | 2/2002 | Finn |
| 6,357,438 B1 | 3/2002 | Hansen |
| 6,357,440 B1 | 3/2002 | Hansen et al. |
| 6,360,741 B2 | 3/2002 | Truschel |
| 6,360,745 B1 | 3/2002 | Wallace et al. |
| 6,363,933 B1 | 4/2002 | Berthon-Jones |
| 6,367,474 B1 | 4/2002 | Berthon-Jones et al. |
| 6,369,838 B1 | 4/2002 | Wallace et al. |
| 6,371,114 B1 | 4/2002 | Schmidt et al. |
| 6,378,520 B1 | 4/2002 | Davenport |
| 6,390,091 B1 | 5/2002 | Banner et al. |
| 6,394,088 B1 | 5/2002 | Frye et al. |
| 6,398,739 B1 | 6/2002 | Sullivan et al. |
| 6,418,928 B1 | 7/2002 | Bordewick et al. |
| 6,422,240 B1 | 7/2002 | Levitsky et al. |
| 6,423,001 B1 | 7/2002 | Abreu |
| 6,427,690 B1 | 8/2002 | McCombs et al. |
| 6,431,172 B1 | 8/2002 | Bordewick |
| 6,439,228 B1 | 8/2002 | Hete et al. |
| 6,439,229 B1 | 8/2002 | Du et al. |
| 6,439,234 B1 | 8/2002 | Curti et al. |
| 6,439,235 B1 | 8/2002 | Larquet et al. |
| 6,450,164 B1 | 9/2002 | Banner et al. |
| 6,450,166 B1 | 9/2002 | McDonald et al. |
| 6,457,472 B1 | 10/2002 | Schwartz et al. |
| 6,467,477 B1 | 10/2002 | Frank et al. |
| 6,478,026 B1 | 11/2002 | Wood |
| 6,494,202 B2 | 12/2002 | Farmer |
| 6,494,206 B1 | 12/2002 | Bergamaschi et al. |
| 6,505,623 B1 | 1/2003 | Hansen |
| 6,505,624 B1 | 1/2003 | Campbell, Sr. |
| 6,516,801 B2 | 2/2003 | Boussignac |
| 6,520,176 B1 | 2/2003 | Dubois et al. |
| 6,520,183 B2 | 2/2003 | Amar |
| 6,530,373 B1 | 3/2003 | Patron et al. |
| 6,532,958 B1 | 3/2003 | Buan et al. |
| 6,532,960 B1 | 3/2003 | Yurko |
| 6,536,432 B2 | 3/2003 | Truschel |
| 6,536,436 B1 | 3/2003 | McGlothen |
| 6,550,478 B2 | 4/2003 | Remmers et al. |
| 6,553,992 B1 | 4/2003 | Berthon-Jones et al. |
| 6,561,188 B1 | 5/2003 | Ellis |
| 6,561,193 B1 | 5/2003 | Noble |
| 6,564,797 B1 | 5/2003 | Mechlenburg et al. |
| 6,564,800 B1 | 5/2003 | Olivares |
| 6,568,391 B1 | 5/2003 | Tatarek et al. |
| 6,571,794 B1 | 6/2003 | Hansen |
| 6,571,796 B2 | 6/2003 | Banner et al. |

(56) References Cited

U.S. PATENT DOCUMENTS

| | | |
|---|---|---|
| 6,571,798 B1 | 6/2003 | Thornton |
| 6,575,159 B1 | 6/2003 | Frye et al. |
| 6,575,944 B1 | 6/2003 | McNary et al. |
| 6,584,973 B1 | 7/2003 | Biondi et al. |
| 6,588,422 B1 | 7/2003 | Berthon-Jones et al. |
| 6,588,423 B1 | 7/2003 | Sinderby |
| 6,591,834 B1 | 7/2003 | Colla et al. |
| 6,591,835 B1 | 7/2003 | Blanch |
| 6,595,207 B1 | 7/2003 | McDonald et al. |
| 6,595,215 B2 | 7/2003 | Wood |
| 6,609,517 B1 | 8/2003 | Estes et al. |
| 6,622,726 B1 | 9/2003 | Du |
| 6,626,174 B1 | 9/2003 | Genger et al. |
| 6,626,175 B2 | 9/2003 | Jafari et al. |
| 6,629,525 B2 | 10/2003 | Hill et al. |
| 6,629,527 B1 | 10/2003 | Estes et al. |
| 6,629,529 B2 | 10/2003 | Arnott |
| 6,631,919 B1 | 10/2003 | West et al. |
| 6,634,356 B1 | 10/2003 | O'Dea et al. |
| 6,635,021 B1 | 10/2003 | Sullivan et al. |
| 6,640,806 B2 | 11/2003 | Yurko |
| 6,644,305 B2 | 11/2003 | MacRae et al. |
| 6,644,311 B1 | 11/2003 | Truitt et al. |
| 6,644,315 B2 | 11/2003 | Ziaee |
| 6,651,653 B1 | 11/2003 | Honkonen et al. |
| 6,651,656 B2 | 11/2003 | Demers et al. |
| 6,651,658 B1 | 11/2003 | Hill et al. |
| 6,655,382 B1 | 12/2003 | Kolobow |
| 6,655,385 B1 | 12/2003 | Curti et al. |
| 6,666,208 B1 | 12/2003 | Schumacher et al. |
| 6,668,828 B1 | 12/2003 | Figley et al. |
| 6,668,829 B2 | 12/2003 | Biondi et al. |
| 6,669,712 B1 | 12/2003 | Cardoso |
| 6,675,796 B2 | 1/2004 | McDonald |
| 6,675,801 B2 | 1/2004 | Wallace et al. |
| 6,679,265 B2 | 1/2004 | Strickland et al. |
| 6,681,764 B1 | 1/2004 | Honkonen et al. |
| 6,684,883 B1 | 2/2004 | Burns |
| 6,691,702 B2 | 2/2004 | Appel et al. |
| 6,691,707 B1 | 2/2004 | Gunaratnam et al. |
| 6,694,973 B1 | 2/2004 | Dunhao et al. |
| 6,694,978 B1 | 2/2004 | Bennarsten |
| 6,698,423 B1 | 3/2004 | Honkonen et al. |
| 6,705,314 B1 | 3/2004 | O'Dea |
| 6,705,315 B2 | 3/2004 | Sullivan et al. |
| 6,722,360 B2 | 4/2004 | Doshi |
| 6,722,362 B2 | 4/2004 | Hete et al. |
| 6,742,517 B1 | 6/2004 | Frye et al. |
| 6,745,768 B2 | 6/2004 | Colla et al. |
| 6,752,150 B1 | 6/2004 | Remmers et al. |
| 6,752,151 B2 | 6/2004 | Hill |
| 6,752,152 B2 | 6/2004 | Gale et al. |
| 6,755,193 B2 | 6/2004 | Berthon-Jones et al. |
| 6,758,217 B1 | 7/2004 | Younes |
| 6,761,172 B2 | 7/2004 | Boussignac et al. |
| 6,763,832 B1 | 7/2004 | Kirsch et al. |
| 6,769,432 B1 | 8/2004 | Keifer |
| 6,776,162 B2 | 8/2004 | Wood |
| 6,776,163 B2 | 8/2004 | Dougill et al. |
| 6,789,539 B2 | 9/2004 | Martinez |
| 6,796,305 B1 | 9/2004 | Banner et al. |
| 6,799,575 B1 | 10/2004 | Carter |
| 6,805,126 B2 | 10/2004 | Dutkiewicz |
| 6,807,966 B2 | 10/2004 | Wright |
| 6,807,967 B2 | 10/2004 | Wood |
| 6,810,876 B2 | 11/2004 | Berthon-Jones |
| 6,814,073 B2 | 11/2004 | Wickham |
| 6,814,077 B1 | 11/2004 | Eistert |
| 6,823,866 B2 | 11/2004 | Jafari et al. |
| 6,827,340 B2 | 12/2004 | Austin et al. |
| 6,837,238 B2 | 1/2005 | McDonald |
| 6,840,240 B1 | 1/2005 | Berthon-Jones et al. |
| 6,843,247 B2 | 1/2005 | Frye et al. |
| 6,848,446 B2 | 2/2005 | Noble |
| 6,854,462 B2 | 2/2005 | Berthon-Jones et al. |
| 6,863,069 B2 | 3/2005 | Wood |
| 6,866,041 B2 | 3/2005 | Hardy, Jr. et al. |
| 6,877,511 B2 | 4/2005 | DeVries et al. |
| 6,880,556 B2 | 4/2005 | Uchiyama et al. |
| 6,910,480 B1 | 6/2005 | Berthon-Jones |
| 6,910,482 B2 | 6/2005 | Bliss et al. |
| 6,910,510 B2 | 6/2005 | Gale et al. |
| 6,913,601 B2 | 7/2005 | St Goar et al. |
| 6,915,803 B2 | 7/2005 | Berthon-Jones et al. |
| 6,920,875 B1 | 7/2005 | Hill et al. |
| 6,920,877 B2 | 7/2005 | Remmers et al. |
| 6,920,878 B2 | 7/2005 | Sinderby et al. |
| 6,932,084 B2 | 8/2005 | Estes et al. |
| 6,938,619 B1 | 9/2005 | Hickle |
| 6,938,620 B2 | 9/2005 | Payne, Jr. |
| 6,941,950 B2 | 9/2005 | Wilson et al. |
| 6,948,497 B2 | 9/2005 | Zdrojkowski et al. |
| 6,951,217 B2 | 10/2005 | Berthon-Jones |
| 6,971,382 B1 | 12/2005 | Corso |
| 6,986,353 B2 | 1/2006 | Wright |
| 6,994,089 B2 | 2/2006 | Wood |
| 6,997,177 B2 | 2/2006 | Wood |
| 6,997,881 B2 | 2/2006 | Green et al. |
| 7,000,612 B2 | 2/2006 | Jafari et al. |
| 7,004,170 B1 | 2/2006 | Gillstrom |
| 7,007,692 B2 | 3/2006 | Aylsworth et al. |
| 7,011,091 B2 | 3/2006 | Hill et al. |
| 7,013,892 B2 | 3/2006 | Estes et al. |
| 7,013,898 B2 | 3/2006 | Rashad et al. |
| 7,017,574 B2 | 3/2006 | Biondi et al. |
| 7,017,575 B2 | 3/2006 | Yagi et al. |
| 7,024,945 B2 | 4/2006 | Wallace |
| 7,036,504 B2 | 5/2006 | Wallace et al. |
| 7,044,129 B1 | 5/2006 | Truschel et al. |
| 7,047,969 B2 | 5/2006 | Noble |
| 7,047,974 B2 | 5/2006 | Strickland et al. |
| 7,051,735 B2 | 5/2006 | Mechlenburg et al. |
| 7,055,522 B2 | 6/2006 | Berthon-Jones |
| 7,059,328 B2 | 6/2006 | Wood |
| 7,066,173 B2 | 6/2006 | Banner et al. |
| 7,066,178 B2 | 6/2006 | Gunaratnam et al. |
| 7,077,132 B2 | 7/2006 | Berthon-Jones |
| 7,077,133 B2 | 7/2006 | Yagi et al. |
| 7,080,645 B2 | 7/2006 | Genger et al. |
| 7,080,646 B2 | 7/2006 | Wiesmann et al. |
| 7,100,607 B2 | 9/2006 | Zdrojkowski et al. |
| 7,100,609 B2 | 9/2006 | Berthon-Jones et al. |
| 7,117,438 B2 | 10/2006 | Wallace et al. |
| 7,121,277 B2 | 10/2006 | Strom |
| 7,128,578 B2 | 10/2006 | Lampotang et al. |
| 7,152,598 B2 | 12/2006 | Morris et al. |
| 7,152,604 B2 | 12/2006 | Hickle et al. |
| 7,156,090 B2 | 1/2007 | Nomori |
| 7,156,097 B2 | 1/2007 | Cardoso |
| 7,162,296 B2 | 1/2007 | Leonhardt et al. |
| 7,168,429 B2 | 1/2007 | Matthews et al. |
| 7,188,621 B2 | 3/2007 | DeVries et al. |
| 7,188,624 B2 | 3/2007 | Wood |
| 7,195,016 B2 | 3/2007 | Loyd et al. |
| 7,195,018 B1 | 3/2007 | Goldstein |
| 7,201,169 B2 | 4/2007 | Wilkie et al. |
| 7,201,269 B2 | 4/2007 | Buscher et al. |
| D542,912 S | 5/2007 | Gunaratnam et al. |
| 7,222,623 B2 | 5/2007 | DeVries et al. |
| 7,225,811 B2 | 6/2007 | Ruiz et al. |
| 7,234,465 B2 | 6/2007 | Wood |
| 7,237,205 B2 | 6/2007 | Sarel |
| 7,246,620 B2 | 7/2007 | Conroy, Jr. |
| D549,323 S | 8/2007 | Kwok et al. |
| 7,255,103 B2 | 8/2007 | Bassin |
| 7,255,107 B1 | 8/2007 | Gomez |
| 7,267,122 B2 | 9/2007 | Hill |
| 7,267,123 B2 | 9/2007 | Aylsworth et al. |
| 7,270,126 B2 | 9/2007 | Wallace et al. |
| 7,270,128 B2 | 9/2007 | Berthon-Jones et al. |
| 7,296,569 B2 | 11/2007 | Frye et al. |
| 7,296,573 B2 | 11/2007 | Estes et al. |
| D557,802 S | 12/2007 | Miceli, Jr. et al. |
| 7,302,950 B2 | 12/2007 | Berthon-Jones et al. |

(56) References Cited

U.S. PATENT DOCUMENTS

| | | | |
|---|---|---|---|
| 7,305,987 B2 | 12/2007 | Scholler et al. |
| 7,318,437 B2 | 1/2008 | Gunaratnam et al. |
| 7,320,321 B2 | 1/2008 | Pranger et al. |
| 7,328,703 B1 | 2/2008 | Tiep |
| 7,353,826 B2 | 4/2008 | Sleeper et al. |
| 7,367,337 B2 | 5/2008 | Berthon-Jones et al. |
| 7,370,652 B2 | 5/2008 | Matula, Jr. et al. |
| 7,373,939 B1 | 5/2008 | DuBois et al. |
| 7,406,966 B2 | 8/2008 | Wondka |
| 7,418,965 B2 | 9/2008 | Fukunaga et al. |
| 7,422,015 B2 | 9/2008 | Delisle et al. |
| 7,431,035 B2 | 10/2008 | Mizuta et al. |
| 7,451,762 B2 | 11/2008 | Chua et al. |
| 7,455,717 B2 | 11/2008 | Sprinkle |
| 7,461,656 B2 | 12/2008 | Gunaratnam et al. |
| 7,468,040 B2 | 12/2008 | Hartley et al. |
| 7,469,697 B2 | 12/2008 | Lee et al. |
| 7,472,702 B2 | 1/2009 | Beck et al. |
| 7,478,641 B2 | 1/2009 | Rousselet |
| 7,481,219 B2 | 1/2009 | Lewis et al. |
| 7,481,221 B2 | 1/2009 | Kullik et al. |
| 7,487,774 B2 | 2/2009 | Acker |
| 7,487,778 B2 | 2/2009 | Freitag |
| 7,490,605 B2 | 2/2009 | Frye et al. |
| D588,258 S | 3/2009 | Judson et al. |
| D589,139 S | 3/2009 | Guney et al. |
| 7,500,482 B2 | 3/2009 | Biederman |
| 7,509,957 B2 | 3/2009 | Duquette et al. |
| D591,419 S | 4/2009 | Chandran et al. |
| 7,533,670 B1 | 5/2009 | Freitag et al. |
| 7,556,038 B2 | 7/2009 | Kirby et al. |
| 7,559,327 B2 | 7/2009 | Hernandez |
| 7,562,657 B2 | 7/2009 | Blanch et al. |
| 7,562,659 B2 | 7/2009 | Matarasso |
| 7,578,294 B2 | 8/2009 | Pierro et al. |
| 7,588,033 B2 | 9/2009 | Wondka |
| 7,591,265 B2 | 9/2009 | Lee et al. |
| 7,617,680 B1 * | 11/2009 | Weaver ............... F01K 25/10 60/517 |
| 7,631,642 B2 | 12/2009 | Freitag et al. |
| 7,640,934 B2 | 1/2010 | Zollinger et al. |
| 7,658,189 B2 | 2/2010 | Davidson et al. |
| D614,288 S | 4/2010 | Judson et al. |
| 7,721,733 B2 | 5/2010 | Hughes et al. |
| 7,721,736 B2 | 5/2010 | Urias et al. |
| 7,740,013 B2 | 6/2010 | Ishizaki et al. |
| 7,743,770 B2 | 6/2010 | Curti et al. |
| 7,762,253 B2 | 7/2010 | Acker et al. |
| 7,766,009 B2 | 8/2010 | Frye et al. |
| 7,787,946 B2 | 8/2010 | Stahmann et al. |
| 7,814,906 B2 | 10/2010 | Moretti |
| 7,819,120 B2 | 10/2010 | Taylor et al. |
| D626,646 S | 11/2010 | Lubke et al. |
| D627,059 S | 11/2010 | Wood et al. |
| 7,832,400 B2 | 11/2010 | Curti et al. |
| 7,837,761 B2 | 11/2010 | Bliss et al. |
| 7,841,343 B2 | 11/2010 | Deane et al. |
| 7,845,350 B1 | 12/2010 | Kayyali et al. |
| 7,849,854 B2 | 12/2010 | DeVries et al. |
| 7,856,982 B2 | 12/2010 | Matula, Jr. et al. |
| 7,866,318 B2 | 1/2011 | Bassin |
| 7,874,290 B2 | 1/2011 | Chalvignac |
| 7,874,291 B2 | 1/2011 | Ging et al. |
| 7,874,293 B2 | 1/2011 | Gunaratnam et al. |
| 7,878,980 B2 | 2/2011 | Ricciardelli |
| 7,882,834 B2 | 2/2011 | Gradon et al. |
| 7,886,740 B2 | 2/2011 | Thomas et al. |
| 7,891,186 B1 * | 2/2011 | Primlani ........................ 60/618 |
| 7,891,353 B2 | 2/2011 | Chalvignac |
| 7,891,357 B2 | 2/2011 | Carron et al. |
| 7,896,958 B2 | 3/2011 | Sermet et al. |
| 7,900,627 B2 | 3/2011 | Aylsworth et al. |
| 7,900,628 B2 | 3/2011 | Matula, Jr. et al. |
| 7,900,635 B2 | 3/2011 | Gunaratnam et al. |
| 7,901,361 B2 | 3/2011 | Rapoport et al. |
| 7,905,231 B2 | 3/2011 | Chalvignac |
| 7,913,691 B2 | 3/2011 | Farrugia |
| 7,914,459 B2 | 3/2011 | Green et al. |
| 7,918,226 B2 | 4/2011 | Acker et al. |
| 7,926,486 B2 | 4/2011 | Childers |
| 7,926,487 B2 | 4/2011 | Drew et al. |
| 7,931,023 B2 | 4/2011 | Berthon-Jones et al. |
| 7,934,499 B2 | 5/2011 | Berthon-Jones |
| 7,938,114 B2 | 5/2011 | Matthews et al. |
| 7,942,150 B2 | 5/2011 | Guney et al. |
| 7,942,380 B2 | 5/2011 | Bertinetti et al. |
| 7,958,892 B2 | 6/2011 | Kwok et al. |
| 7,975,694 B2 | 7/2011 | Ho |
| 7,980,245 B2 | 7/2011 | Rice et al. |
| 7,987,847 B2 | 8/2011 | Wickham et al. |
| 7,987,850 B2 | 8/2011 | Zollinger et al. |
| 7,987,851 B2 | 8/2011 | Blom et al. |
| 7,992,557 B2 | 8/2011 | Nadjafizadeh et al. |
| 7,997,270 B2 | 8/2011 | Meier |
| 7,997,271 B2 | 8/2011 | Hickle et al. |
| 7,997,272 B2 | 8/2011 | Isaza |
| 8,001,967 B2 | 8/2011 | Wallace et al. |
| D645,557 S | 9/2011 | Scheiner et al. |
| 8,011,365 B2 | 9/2011 | Douglas et al. |
| 8,011,366 B2 | 9/2011 | Knepper |
| 8,015,971 B2 | 9/2011 | Kwok |
| 8,015,974 B2 | 9/2011 | Christopher et al. |
| 8,020,558 B2 | 9/2011 | Christopher et al. |
| 8,025,052 B2 | 9/2011 | Matthews et al. |
| RE42,843 E | 10/2011 | Strickland et al. |
| 8,042,535 B2 | 10/2011 | Kenyon et al. |
| 8,042,537 B2 | 10/2011 | Mechlenburg et al. |
| 8,042,539 B2 | 10/2011 | Chandran et al. |
| 8,042,546 B2 | 10/2011 | Gunaratnam et al. |
| 8,061,354 B2 | 11/2011 | Schneider et al. |
| 8,066,004 B2 | 11/2011 | Morris et al. |
| 2001/0035185 A1 | 11/2001 | Christopher |
| 2001/0035186 A1 | 11/2001 | Hill |
| 2001/0042548 A1 | 11/2001 | Boussignac |
| 2002/0014241 A1 | 2/2002 | Gradon et al. |
| 2002/0017300 A1 | 2/2002 | Hickle et al. |
| 2002/0020930 A1 | 2/2002 | Austin et al. |
| 2002/0026941 A1 | 3/2002 | Biondi et al. |
| 2002/0043264 A1 | 4/2002 | Wickham |
| 2002/0046751 A1 | 4/2002 | MacRae et al. |
| 2002/0046755 A1 | 4/2002 | De Voss |
| 2002/0046756 A1 | 4/2002 | Laizzo et al. |
| 2002/0053346 A1 | 5/2002 | Curti et al. |
| 2002/0055685 A1 | 5/2002 | Levitsky et al. |
| 2002/0059935 A1 | 5/2002 | Wood |
| 2002/0066452 A1 | 6/2002 | Kessler et al. |
| 2002/0078957 A1 | 6/2002 | Remmers et al. |
| 2002/0092527 A1 | 7/2002 | Wood |
| 2002/0112730 A1 | 8/2002 | Dutkiewicz |
| 2002/0153010 A1 | 10/2002 | Rozenberg et al. |
| 2002/0157673 A1 | 10/2002 | Kessler et al. |
| 2002/0159323 A1 | 10/2002 | Makabe et al. |
| 2002/0179090 A1 | 12/2002 | Boussignac |
| 2003/0000522 A1 | 1/2003 | Lynn et al. |
| 2003/0005928 A1 | 1/2003 | Appel et al. |
| 2003/0046932 A1 * | 3/2003 | Isaac et al. ...................... 60/643 |
| 2003/0047185 A1 | 3/2003 | Olsen et al. |
| 2003/0069489 A1 | 4/2003 | Abreu |
| 2003/0079749 A1 | 5/2003 | Strickland et al. |
| 2003/0094178 A1 | 5/2003 | McAuley et al. |
| 2003/0111081 A1 | 6/2003 | Gupta |
| 2003/0116163 A1 | 6/2003 | Wood |
| 2003/0121519 A1 | 7/2003 | Estes et al. |
| 2003/0145852 A1 | 8/2003 | Schmidt et al. |
| 2003/0145853 A1 | 8/2003 | Muellner |
| 2003/0145856 A1 | 8/2003 | Zdrojkowski et al. |
| 2003/0150455 A1 | 8/2003 | Bliss et al. |
| 2003/0159696 A1 | 8/2003 | Boussignac et al. |
| 2003/0159697 A1 | 8/2003 | Wallace |
| 2003/0168067 A1 | 9/2003 | Dougill et al. |
| 2003/0213488 A1 | 11/2003 | Remmers et al. |
| 2003/0221687 A1 | 12/2003 | Kaigler |
| 2003/0230308 A1 | 12/2003 | Linden |
| 2004/0020493 A1 | 2/2004 | Wood |

(56) References Cited

U.S. PATENT DOCUMENTS

| | | |
|---|---|---|
| 2004/0025881 A1 | 2/2004 | Gunaratnam et al. |
| 2004/0035431 A1 | 2/2004 | Wright |
| 2004/0040560 A1 | 3/2004 | Euliano et al. |
| 2004/0050387 A1 | 3/2004 | Younes |
| 2004/0074494 A1 | 4/2004 | Frater |
| 2004/0089336 A1* | 5/2004 | Hunt .................. H01L 35/30 136/205 |
| 2004/0159323 A1 | 8/2004 | Schmidt et al. |
| 2004/0206352 A1 | 10/2004 | Conroy |
| 2004/0221848 A1 | 11/2004 | Hill |
| 2004/0221854 A1 | 11/2004 | Hete et al. |
| 2004/0226566 A1 | 11/2004 | Gunaratnam et al. |
| 2004/0231674 A1 | 11/2004 | Tanaka |
| 2004/0237963 A1 | 12/2004 | Berthon-Jones |
| 2004/0254501 A1 | 12/2004 | Mault |
| 2004/0255943 A1 | 12/2004 | Morris et al. |
| 2005/0005938 A1 | 1/2005 | Berthon-Jones et al. |
| 2005/0010125 A1 | 1/2005 | Joy et al. |
| 2005/0011524 A1 | 1/2005 | Thomlinson et al. |
| 2005/0016534 A1 | 1/2005 | Ost |
| 2005/0033247 A1 | 2/2005 | Thompson |
| 2005/0034724 A1 | 2/2005 | O'Dea |
| 2005/0061322 A1 | 3/2005 | Freitag |
| 2005/0061326 A1 | 3/2005 | Payne |
| 2005/0072430 A1 | 4/2005 | Djupesland |
| 2005/0081849 A1 | 4/2005 | Warren |
| 2005/0087190 A1 | 4/2005 | Jafari et al. |
| 2005/0098179 A1 | 5/2005 | Burton et al. |
| 2005/0103343 A1 | 5/2005 | Gosweiler |
| 2005/0121033 A1 | 6/2005 | Starr et al. |
| 2005/0121037 A1 | 6/2005 | Wood |
| 2005/0121038 A1 | 6/2005 | Christopher |
| 2005/0150498 A1 | 7/2005 | McDonald |
| 2005/0161049 A1 | 7/2005 | Wright |
| 2005/0166924 A1 | 8/2005 | Thomas et al. |
| 2005/0199242 A1 | 9/2005 | Matula et al. |
| 2005/0205096 A1 | 9/2005 | Matula et al. |
| 2005/0247308 A1 | 11/2005 | Frye et al. |
| 2005/0257793 A1 | 11/2005 | Tatsumoto |
| 2005/0274381 A1 | 12/2005 | Deane et al. |
| 2006/0005834 A1 | 1/2006 | Aylsworth et al. |
| 2006/0005842 A1 | 1/2006 | Rashad et al. |
| 2006/0011199 A1 | 1/2006 | Rashad et al. |
| 2006/0027234 A1 | 2/2006 | Gradon et al. |
| 2006/0032228 A1* | 2/2006 | Marin et al. .................. 60/730 |
| 2006/0048781 A1 | 3/2006 | Nawata |
| 2006/0054169 A1 | 3/2006 | Han et al. |
| 2006/0070625 A1 | 4/2006 | Ayappa et al. |
| 2006/0079799 A1 | 4/2006 | Green et al. |
| 2006/0096596 A1 | 5/2006 | Occhialini et al. |
| 2006/0107958 A1 | 5/2006 | Sleeper |
| 2006/0112959 A1 | 6/2006 | Mechlenburg et al. |
| 2006/0117646 A1* | 6/2006 | Dai .................. A01M 1/023 43/139 |
| 2006/0118274 A1* | 6/2006 | Lee et al. .................. 165/58 |
| 2006/0124131 A1 | 6/2006 | Chandran et al. |
| 2006/0124134 A1 | 6/2006 | Wood |
| 2006/0137690 A1 | 6/2006 | Gunaratnam et al. |
| 2006/0144396 A1 | 7/2006 | DeVries et al. |
| 2006/0149144 A1 | 7/2006 | Lynn et al. |
| 2006/0150972 A1 | 7/2006 | Mizuta et al. |
| 2006/0150973 A1 | 7/2006 | Chalvignac |
| 2006/0150982 A1 | 7/2006 | Wood |
| 2006/0174877 A1 | 8/2006 | Jagger et al. |
| 2006/0180149 A1 | 8/2006 | Matarasso |
| 2006/0185669 A1 | 8/2006 | Bassovitch |
| 2006/0201504 A1 | 9/2006 | Singhal et al. |
| 2006/0213518 A1 | 9/2006 | DeVries et al. |
| 2006/0213519 A1 | 9/2006 | Schmidt et al. |
| 2006/0225737 A1 | 10/2006 | Lobbi |
| 2006/0237013 A1 | 10/2006 | Kwok |
| 2006/0243278 A1 | 11/2006 | Hamilton et al. |
| 2006/0249155 A1 | 11/2006 | Gambone |
| 2006/0266361 A1 | 11/2006 | Hernandez |
| 2006/0288709 A1* | 12/2006 | Reidy .................. 62/3.4 |
| 2007/0000490 A1 | 1/2007 | DeVries et al. |
| 2007/0000495 A1 | 1/2007 | Matula et al. |
| 2007/0017515 A1 | 1/2007 | Wallace et al. |
| 2007/0056590 A1 | 3/2007 | Wolfson |
| 2007/0062529 A1 | 3/2007 | Choncholas et al. |
| 2007/0068528 A1 | 3/2007 | Bohm et al. |
| 2007/0074724 A1 | 4/2007 | Duquette et al. |
| 2007/0089743 A1 | 4/2007 | Hoffman |
| 2007/0089745 A1 | 4/2007 | Gabriel et al. |
| 2007/0095347 A1 | 5/2007 | Lampotang et al. |
| 2007/0107728 A1 | 5/2007 | Ricciardelli et al. |
| 2007/0107732 A1 | 5/2007 | Dennis et al. |
| 2007/0107737 A1 | 5/2007 | Landis et al. |
| 2007/0113850 A1 | 5/2007 | Acker et al. |
| 2007/0113856 A1 | 5/2007 | Acker et al. |
| 2007/0125379 A1 | 6/2007 | Pierro et al. |
| 2007/0137653 A1 | 6/2007 | Wood |
| 2007/0163600 A1 | 7/2007 | Hoffman |
| 2007/0173705 A1 | 7/2007 | Teller et al. |
| 2007/0181125 A1 | 8/2007 | Mulier |
| 2007/0193705 A1 | 8/2007 | Hsu |
| 2007/0199568 A1 | 8/2007 | Diekens et al. |
| 2007/0209662 A1 | 9/2007 | Bowen et al. |
| 2007/0215156 A1 | 9/2007 | Kwok |
| 2007/0232950 A1 | 10/2007 | West |
| 2007/0240716 A1 | 10/2007 | Marx |
| 2007/0240862 A1 | 10/2007 | Baudat et al. |
| 2007/0251528 A1 | 11/2007 | Seitz et al. |
| 2007/0272249 A1 | 11/2007 | Chandran et al. |
| 2007/0289300 A1* | 12/2007 | Lin .................. F02G 1/043 60/517 |
| 2008/0000475 A1 | 1/2008 | Hill |
| 2008/0006271 A1 | 1/2008 | Aylsworth et al. |
| 2008/0011298 A1 | 1/2008 | Mazar et al. |
| 2008/0011301 A1 | 1/2008 | Qian |
| 2008/0041371 A1 | 2/2008 | Freitag |
| 2008/0041386 A1 | 2/2008 | Dodier et al. |
| 2008/0045815 A1 | 2/2008 | Derchak et al. |
| 2008/0047559 A1 | 2/2008 | Fiori |
| 2008/0051674 A1 | 2/2008 | Davenport et al. |
| 2008/0053438 A1 | 3/2008 | DeVries et al. |
| 2008/0053447 A1 | 3/2008 | Ratajczak et al. |
| 2008/0060646 A1 | 3/2008 | Isaza |
| 2008/0060657 A1 | 3/2008 | McAuley et al. |
| 2008/0066753 A1 | 3/2008 | Martin et al. |
| 2008/0072902 A1 | 3/2008 | Setzer et al. |
| 2008/0078392 A1 | 4/2008 | Pelletier et al. |
| 2008/0078407 A1 | 4/2008 | Sherman |
| 2008/0092904 A1 | 4/2008 | Gunarathnam et al. |
| 2008/0092905 A1 | 4/2008 | Gunarathnam et al. |
| 2008/0092906 A1 | 4/2008 | Gunarathnam et al. |
| 2008/0099024 A1 | 5/2008 | Gunarathnam et al. |
| 2008/0099027 A1 | 5/2008 | Gunaratnam et al. |
| 2008/0105264 A1 | 5/2008 | Gunarathnam et al. |
| 2008/0110462 A1 | 5/2008 | Chekal et al. |
| 2008/0121230 A1 | 5/2008 | Cortez et al. |
| 2008/0134690 A1 | 6/2008 | Reid |
| 2008/0135044 A1* | 6/2008 | Freitag et al. .................. 128/200.26 |
| 2008/0142019 A1 | 6/2008 | Lewis et al. |
| 2008/0151499 A1* | 6/2008 | Tsai .................. G06F 1/20 361/697 |
| 2008/0161653 A1 | 7/2008 | Lin et al. |
| 2008/0173304 A1 | 7/2008 | Zaiser et al. |
| 2008/0178880 A1 | 7/2008 | Christopher et al. |
| 2008/0178881 A1 | 7/2008 | Whitcher et al. |
| 2008/0178882 A1 | 7/2008 | Christopher et al. |
| 2008/0185002 A1 | 8/2008 | Berthon-Jones et al. |
| 2008/0185007 A1 | 8/2008 | Sleeper et al. |
| 2008/0190429 A1 | 8/2008 | Tatarek |
| 2008/0190436 A1 | 8/2008 | Jaffe et al. |
| 2008/0196305 A1* | 8/2008 | Gerfast .................. C10J 3/30 48/73 |
| 2008/0196715 A1 | 8/2008 | Yamamori |
| 2008/0196723 A1 | 8/2008 | Tilley |
| 2008/0196728 A1 | 8/2008 | Ho |
| 2008/0202528 A1 | 8/2008 | Carter et al. |
| 2008/0216834 A1 | 9/2008 | Easley et al. |
| 2008/0216838 A1 | 9/2008 | Wondka |
| 2008/0216841 A1 | 9/2008 | Grimes et al. |

(56) References Cited

U.S. PATENT DOCUMENTS

| | | |
|---|---|---|
| 2008/0223369 A1 | 9/2008 | Warren |
| 2008/0245369 A1 | 10/2008 | Matula et al. |
| 2008/0251079 A1 | 10/2008 | Richey |
| 2008/0264417 A1 | 10/2008 | Manigel et al. |
| 2008/0283060 A1 | 11/2008 | Bassin |
| 2008/0295846 A1 | 12/2008 | Han et al. |
| 2008/0302364 A1 | 12/2008 | Garde et al. |
| 2008/0308104 A1 | 12/2008 | Blomberg et al. |
| 2009/0007911 A1 | 1/2009 | Cleary et al. |
| 2009/0019886 A1* | 1/2009 | Willen .................. F25J 1/0208 62/606 |
| 2009/0020121 A1 | 1/2009 | Bassin |
| 2009/0044808 A1 | 2/2009 | Guney et al. |
| 2009/0056708 A1 | 3/2009 | Stenzler et al. |
| 2009/0077970 A1* | 3/2009 | Da Costa ................ F01K 25/10 60/650 |
| 2009/0078255 A1 | 3/2009 | Bowman et al. |
| 2009/0078258 A1 | 3/2009 | Bowman et al. |
| 2009/0095298 A1 | 4/2009 | Gunaratnam et al. |
| 2009/0095300 A1 | 4/2009 | McMorrow |
| 2009/0095303 A1 | 4/2009 | Sher et al. |
| 2009/0099471 A1 | 4/2009 | Broadley et al. |
| 2009/0101147 A1 | 4/2009 | Landis et al. |
| 2009/0101154 A1 | 4/2009 | Mutti et al. |
| 2009/0107502 A1 | 4/2009 | Younes |
| 2009/0118632 A1 | 5/2009 | Goepp |
| 2009/0120437 A1 | 5/2009 | Oates et al. |
| 2009/0126372 A1* | 5/2009 | Faka .......................... F17C 7/04 62/50.2 |
| 2009/0126739 A1 | 5/2009 | Ng et al. |
| 2009/0133699 A1 | 5/2009 | Nalagatla et al. |
| 2009/0139527 A1 | 6/2009 | Ng et al. |
| 2009/0145435 A1 | 6/2009 | White et al. |
| 2009/0151719 A1 | 6/2009 | Wondka et al. |
| 2009/0151724 A1 | 6/2009 | Wondka et al. |
| 2009/0151726 A1 | 6/2009 | Freitag |
| 2009/0151729 A1 | 6/2009 | Judson et al. |
| 2009/0156953 A1 | 6/2009 | Wondka et al. |
| 2009/0165799 A1 | 7/2009 | Duquette et al. |
| 2009/0173347 A1 | 7/2009 | Berthon-Jones |
| 2009/0173349 A1 | 7/2009 | Hernandez et al. |
| 2009/0183739 A1 | 7/2009 | Wondka |
| 2009/0199855 A1 | 8/2009 | Davenport |
| 2009/0205662 A1 | 8/2009 | Kwok et al. |
| 2009/0241947 A1 | 10/2009 | Bedini et al. |
| 2009/0241951 A1 | 10/2009 | Jafari et al. |
| 2009/0250066 A1 | 10/2009 | Daly |
| 2009/0255533 A1 | 10/2009 | Freitag et al. |
| 2009/0260625 A1 | 10/2009 | Wondka |
| 2009/0277452 A1 | 11/2009 | Lubke et al. |
| 2009/0293877 A1 | 12/2009 | Blanch et al. |
| 2009/0301495 A1 | 12/2009 | Pierro et al. |
| 2009/0308395 A1 | 12/2009 | Lee et al. |
| 2009/0320851 A1 | 12/2009 | Selvarajan et al. |
| 2010/0043786 A1 | 2/2010 | Freitag et al. |
| 2010/0071693 A1 | 3/2010 | Allum et al. |
| 2010/0071697 A1 | 3/2010 | Jafari et al. |
| 2010/0083968 A1 | 4/2010 | Wondka et al. |
| 2010/0108063 A1* | 5/2010 | Koch ................ A61M 16/1075 128/204.15 |
| 2010/0108073 A1 | 5/2010 | Zollinger et al. |
| 2010/0132716 A1 | 6/2010 | Selvarajan et al. |
| 2010/0132717 A1 | 6/2010 | Davidson et al. |
| 2010/0163043 A1 | 7/2010 | Hart et al. |
| 2010/0170512 A1 | 7/2010 | Kuypers et al. |
| 2010/0170513 A1 | 7/2010 | Bowditch et al. |
| 2010/0192957 A1 | 8/2010 | Hobson et al. |
| 2010/0218766 A1 | 9/2010 | Milne |
| 2010/0224196 A1 | 9/2010 | Jablons |
| 2010/0252037 A1 | 10/2010 | Wondka et al. |
| 2010/0252039 A1 | 10/2010 | Cipollone et al. |
| 2010/0252040 A1 | 10/2010 | Kapust et al. |
| 2010/0252041 A1 | 10/2010 | Kapust et al. |
| 2010/0252042 A1 | 10/2010 | Kapust et al. |
| 2010/0252043 A1 | 10/2010 | Freitag |
| 2010/0252044 A1 | 10/2010 | Duquette et al. |
| 2010/0269834 A1 | 10/2010 | Freitag et al. |
| 2010/0275920 A1 | 11/2010 | Tham et al. |
| 2010/0275921 A1 | 11/2010 | Schindhelm et al. |
| 2010/0282251 A1 | 11/2010 | Calluaud et al. |
| 2010/0282810 A1 | 11/2010 | Hawes |
| 2010/0288279 A1 | 11/2010 | Seiver et al. |
| 2010/0288289 A1 | 11/2010 | Nasir |
| 2010/0300445 A1 | 12/2010 | Chatburn et al. |
| 2010/0300446 A1 | 12/2010 | Nicolazzi et al. |
| 2010/0300663 A1* | 12/2010 | Tso et al. ...................... 165/135 |
| 2010/0307487 A1 | 12/2010 | Dunsmore et al. |
| 2010/0307495 A1 | 12/2010 | Kepler et al. |
| 2010/0307499 A1 | 12/2010 | Eger et al. |
| 2010/0307500 A1 | 12/2010 | Armitstead |
| 2010/0307502 A1 | 12/2010 | Rummery et al. |
| 2010/0313891 A1 | 12/2010 | Veliss et al. |
| 2010/0313898 A1 | 12/2010 | Richard et al. |
| 2010/0319703 A1 | 12/2010 | Hayman et al. |
| 2010/0326441 A1 | 12/2010 | Zucker et al. |
| 2010/0326446 A1 | 12/2010 | Behlmaier |
| 2011/0000489 A1 | 1/2011 | Laksov et al. |
| 2011/0009763 A1 | 1/2011 | Levitsky et al. |
| 2011/0011402 A1 | 1/2011 | Berthon-Jones |
| 2011/0023878 A1 | 2/2011 | Thiessen |
| 2011/0023881 A1 | 2/2011 | Thiessen |
| 2011/0034819 A1 | 2/2011 | Desforges et al. |
| 2011/0036352 A1 | 2/2011 | Estes et al. |
| 2011/0041850 A1 | 2/2011 | Vandine et al. |
| 2011/0041855 A1 | 2/2011 | Gunaratnam et al. |
| 2011/0061647 A1 | 3/2011 | Stahmann et al. |
| 2011/0067704 A1 | 3/2011 | Kooij et al. |
| 2011/0067709 A1 | 3/2011 | Doshi et al. |
| 2011/0071444 A1 | 3/2011 | Kassatly et al. |
| 2011/0073107 A1 | 3/2011 | Rodman et al. |
| 2011/0073116 A1 | 3/2011 | Genger et al. |
| 2011/0087123 A9 | 4/2011 | Choncholas et al. |
| 2011/0088690 A1 | 4/2011 | Djupesland et al. |
| 2011/0094518 A1 | 4/2011 | Cipollone et al. |
| 2011/0100365 A1 | 5/2011 | Wedler et al. |
| 2011/0114098 A1 | 5/2011 | McAuley et al. |
| 2011/0125052 A1 | 5/2011 | Davenport et al. |
| 2011/0126841 A1 | 6/2011 | Matula, Jr. et al. |
| 2011/0132363 A1 | 6/2011 | Chalvignac |
| 2011/0139153 A1 | 6/2011 | Chalvignac |
| 2011/0146687 A1 | 6/2011 | Fukushima |
| 2011/0155140 A1 | 6/2011 | Ho et al. |
| 2011/0162650 A1 | 7/2011 | Miller et al. |
| 2011/0162655 A1 | 7/2011 | Gunaratnam et al. |
| 2011/0178419 A1 | 7/2011 | Wood et al. |
| 2011/0180068 A1 | 7/2011 | Kenyon et al. |
| 2011/0187019 A1* | 8/2011 | Hackl ................. B29C 47/0023 264/234 |
| 2011/0197885 A1 | 8/2011 | Wondka et al. |
| 2011/0203311 A1* | 8/2011 | Wright .................... B01D 53/02 62/602 |
| 2011/0209705 A1 | 9/2011 | Freitag |
| 2011/0214676 A1 | 9/2011 | Allum et al. |
| 2011/0220105 A1 | 9/2011 | Meier |
| 2011/0225987 A1* | 9/2011 | Bowdish ................... F17C 9/04 62/50.3 |
| 2011/0232642 A1 | 9/2011 | Bliss et al. |
| 2011/0247625 A1 | 10/2011 | Boussignac |
| 2011/0253147 A1 | 10/2011 | Gusky et al. |
| 2011/0259327 A1 | 10/2011 | Wondka et al. |
| 2011/0265796 A1 | 11/2011 | Amarasinghe et al. |
| 2011/0277765 A1 | 11/2011 | Christopher et al. |
| 2011/0284003 A1 | 11/2011 | Douglas et al. |

FOREIGN PATENT DOCUMENTS

| | | |
|---|---|---|
| DE | 19841070 | 5/2000 |
| DE | 19849571 | 5/2000 |
| DE | 10337138.9 | 3/2005 |
| DE | 10 2006 023 637.8 | 11/2007 |
| EP | 0125424 | 11/1984 |
| EP | 0692273 | 1/1996 |
| EP | 0778035 | 6/1997 |
| EP | 1359961 | 11/2003 |

(56) References Cited

FOREIGN PATENT DOCUMENTS

| | | | | |
|---|---|---|---|---|
| EP | 1992382 A1 | 11/2008 | | |
| EP | 2377462 | 11/2010 | | |
| GB | 2174609 | 11/1986 | | |
| GB | 2201098 | 8/1988 | | |
| GB | 1055148 | 6/1989 | | |
| GB | 2338420 | 12/1999 | | |
| IT | 2123968 A1 * | 11/2009 | ............ | F01K 23/00 |
| JP | S616656 | 1/1986 | | |
| JP | S63-57060 | 3/1998 | | |
| JP | 2002-204830 | 7/2002 | | |
| JP | 2009545384 | 12/2009 | | |
| WO | WO-1992/11054 | 7/1992 | | |
| WO | WO-1998/01176 | 1/1998 | | |
| WO | 9858219 A1 | 12/1998 | | |
| WO | WO-1999/04841 | 2/1999 | | |
| WO | WO-2000/064521 | 11/2000 | | |
| WO | WO-2001/076655 | 10/2001 | | |
| WO | WO 2002/062413 | 8/2002 | | |
| WO | WO-2004/009169 | 1/2004 | | |
| WO | WO-2005/014091 | 2/2005 | | |
| WO | WO-2005/018524 | 3/2005 | | |
| WO | 2006096450 A2 | 9/2006 | | |
| WO | WO-2006/138580 | 12/2006 | | |
| WO | WO-2007/035804 | 3/2007 | | |
| WO | WO-2007/139531 | 12/2007 | | |
| WO | WO-2007142812 | 12/2007 | | |
| WO | WO-2008/014543 | 2/2008 | | |
| WO | WO-2008/019102 | 2/2008 | | |
| WO | WO-2008/052534 | 5/2008 | | |
| WO | WO-2008/112474 | 9/2008 | | |
| WO | WO-2008/138040 | 11/2008 | | |
| WO | WO-2008/144589 | 11/2008 | | |
| WO | WO-2008/144669 | 11/2008 | | |
| WO | WO-2009/042973 | 4/2009 | | |
| WO | WO-2009/042974 | 4/2009 | | |
| WO | WO-2009/059353 | 5/2009 | | |
| WO | WO-2009/064202 | 5/2009 | | |
| WO | WO-2009/074160 | 6/2009 | | |
| WO | WO-2009/082295 | 7/2009 | | |
| WO | WO-2009/087607 | 7/2009 | | |
| WO | WO-2009/092057 | 7/2009 | | |
| WO | WO-2009/103288 | 8/2009 | | |
| WO | WO-2009/109005 | 9/2009 | | |
| WO | WO-2009/115944 | 9/2009 | | |
| WO | WO-2009/115948 | 9/2009 | | |
| WO | WO-2009/115949 | 9/2009 | | |
| WO | WO-2009/129506 | 10/2009 | | |
| WO | WO-2009/136101 | 11/2009 | | |
| WO | WO-2009/139647 | 11/2009 | | |
| WO | WO-2009/149351 | 12/2009 | | |
| WO | WO-2009/149353 | 12/2009 | | |
| WO | WO-2009/149355 | 12/2009 | | |
| WO | WO-2009/149357 | 12/2009 | | |
| WO | WO-2009/151344 | 12/2009 | | |
| WO | WO-2009/151791 | 12/2009 | | |
| WO | WO-2010/000135 | 1/2010 | | |
| WO | WO-2010/021556 | 2/2010 | | |
| WO | WO-2010/022363 | 2/2010 | | |
| WO | WO-2010/039989 | 4/2010 | | |
| WO | WO-2010/041966 | 4/2010 | | |
| WO | WO-2010/044034 | 4/2010 | | |
| WO | WO-2010/057268 | 5/2010 | | |
| WO | WO-2010/059049 | 5/2010 | | |
| WO | WO-2010/060422 | 6/2010 | | |
| WO | WO-2010/068356 | 6/2010 | | |
| WO | WO-2010/070493 | 6/2010 | | |
| WO | WO-2010/070497 | 6/2010 | | |
| WO | WO-2010/070498 | 6/2010 | | |
| WO | WO-2010/076711 | 7/2010 | | |
| WO | WO-2010/081223 | 7/2010 | | |
| WO | WO-2010/091157 | 8/2010 | | |
| WO | WO 2010/099375 | 9/2010 | | |
| WO | WO-2010/102094 | 9/2010 | | |
| WO | WO 2010/115166 | 10/2010 | | |
| WO | WO 2010/115168 | 10/2010 | | |
| WO | WO 2010/115169 | 10/2010 | | |
| WO | WO 2010/115170 | 10/2010 | | |
| WO | WO-2010/116275 | 10/2010 | | |
| WO | WO-2010/132853 | 11/2010 | | |
| WO | WO-2010/136923 | 12/2010 | | |
| WO | WO-2010/139014 | 12/2010 | | |
| WO | WO-2010/150187 | 12/2010 | | |
| WO | WO 2011/002608 | 1/2011 | | |
| WO | WO-2011/004274 | 1/2011 | | |
| WO | WO-2011/006184 | 1/2011 | | |
| WO | WO-2011/006199 | 1/2011 | | |
| WO | WO-2011/014931 | 2/2011 | | |
| WO | WO-2011/017033 | 2/2011 | | |
| WO | WO-2011/017738 | 2/2011 | | |
| WO | WO-2011/021978 | 2/2011 | | |
| WO | WO-2011/022779 | 3/2011 | | |
| WO | WO-2011/024383 | 3/2011 | | |
| WO | WO 2011/029073 | 3/2011 | | |
| WO | WO 2011/029074 | 3/2011 | | |
| WO | WO-2011/035373 | 3/2011 | | |
| WO | WO-2011/038950 | 4/2011 | | |
| WO | WO-2011/038951 | 4/2011 | | |
| WO | WO-2011/044627 | 4/2011 | | |
| WO | WO-2011/057362 | 5/2011 | | |
| WO | WO 2011/059346 | 5/2011 | | |
| WO | WO-2011/061648 | 5/2011 | | |
| WO | WO-2011/062510 | 5/2011 | | |
| WO | WO-2011/086437 | 7/2011 | | |
| WO | WO-2011/086438 | 7/2011 | | |
| WO | WO-2011/112807 | 9/2011 | | |

OTHER PUBLICATIONS

In the U.S. Patent and Trademark Office, Supplemental Notice of Allowance dated in re: U.S. Appl. No. 10/771,803, dated Nov. 7, 2008, 2 pages.
In the U.S. Patent and Trademark Office, Examiner's Interview Summary in re: U.S. Appl. No. 10/771,803, dated Oct. 31, 2008, 4 pages.
In the U.S. Patent and Trademark Office, Notice of Allowance dated in re: U.S. Appl. No. 10/771,803, dated Oct. 20, 2008, 8 pages.
In the U.S. Patent and Trademark Office, Examiner's Interview Summary in re: U.S. Appl. No. 10/771,803, dated Nov. 2, 2007, 2 pages.
In the U.S. Patent and Trademark Office, Office Action in re: U.S. Appl. No. 10/771,803, dated Jun. 14, 2007, 12 pages.
In the U.S. Patent and Trademark Office, Restriction Requirement in re: U.S. Appl. No. 12/271,484, dated Feb. 9, 2011, 5 pages.
In the U.S. Patent and Trademark Office, Restriction Requirement in re: U.S. Appl. No. 12/754,437, dated Aug. 16, 2011, 5 pages.
In the U.S. Patent and Trademark Office, Non-Final Office Action dated in re: U.S. Appl. No. 10/567,746, dated Oct. 5, 2009, 9 pages.
In the U.S. Patent and Trademark Office, Notice of Allowance and Examiner's Interview Summary in re: U.S. Appl. No. 11/523,519, dated Jan. 16, 2009, 10 pages.
In the U.S. Patent and Trademark Office, Examiner's Interview Summary in re: U.S. Appl. No. 11/523,519, dated Jan. 13, 2009, 4 pages.
In the U.S. Patent and Trademark Office, Final Office Action in re: U.S. Appl. No. 11/523,519, dated Jul. 11, 2008, 13 pages.
In the U.S. Patent and Trademark Office, Examiner's Interview Summary in re: U.S. Appl. No. 11/523,519, dated Apr. 10, 2008, 3 pages.
In the U.S. Patent and Trademark Office, Final Office Action in re: U.S. Appl. No. 11/523,519, dated Nov. 26, 2007, 14 pages.
In the U.S. Patent and Trademark Office, Office Action in re: U.S. Appl. No. 11/523,519, dated Mar. 7, 2007, 11 pages.
In the U.S. Patent and Trademark Office, Restriction Requirement in re: U.S. Appl. No. 11/523,518, dated Dec. 30, 2009, 4 pages.
In the U.S. Patent and Trademark Office, Supplemental Notice of Allowance in re: U.S. Appl. No. 11/798,965, dated Aug. 21, 2009, 4 pages.
In the U.S. Patent and Trademark Office, Notice of Allowance in re: U.S. Appl. No. 11/798,965, dated Jul. 17, 2009, 5 pages.

(56) References Cited

OTHER PUBLICATIONS

In the U.S. Patent and Trademark Office, Final Office Action in re: U.S. Appl. No. 11/798,965, dated Apr. 9, 2009, 6 pages.
In the U.S. Patent and Trademark Office, Office Action in re: U.S. Appl. No. 11/798,965, dated Jul. 29, 2008, 12 pages.
In the U.S. Patent and Trademark Office, Office Action in re: U.S. Appl. No. 12/578,283, dated Oct. 19, 2011, 5 pages.
In the U.S. Patent and Trademark Office, Restriction/Election Requirement in re: U.S. Appl. No. 11/882,530, dated Apr. 27, 2011, 5 pages.
In the U.S. Patent and Trademark Office, Supplemental Notice of Allowance in re: U.S. Appl. No. 10/870,849, dated Jun. 16, 2009, 2 pages.
In the U.S. Patent and Trademark Office, Notice of Allowance in re: U.S. Appl. No. 10/870,849, dated Jun. 3, 2009, 4 pages.
In the U.S. Patent and Trademark Office, Notice of Allowance in re: U.S. Appl. No. 10/870,849, dated May 14, 2009, 8 pages.
In the U.S. Patent and Trademark Office, Restriction in re: U.S. Appl. No. 10/870,849, dated Nov. 16, 2007, 5 pages.
In the U.S. Patent and Trademark Office, Examiner's Interview Summary in re: U.S. Appl. No. 10/870,849, dated Jul. 27, 2007, 2 pages.
In the U.S. Patent and Trademark Office, Office Action in re: U.S. Appl. No. 10/870,849, dated Feb. 22, 2007, 13 pages.
In the U.S. Patent and Trademark Office, Restriction/Election Requirement in re: U.S. Appl. No. 12/493,677, dated Aug. 5, 2011, 5 pages.
In the U.S. Patent and Trademark Office, Restriction/Election Requirement in re: U.S. Appl. No. 12/153,423, dated Oct. 6, 2011, 8 pages.
In the U.S. Patent and Trademark Office, Notice of Allowance in re: U.S. Appl. No. 10/922,054, dated Feb. 12, 2008, 6 pages.
In the U.S. Patent and Trademark Office, Final Office Action in re: U.S. Appl. No. 10/922,054, dated Nov. 27, 2007, 9 pages.
In the U.S. Patent and Trademark Office, Office Action in re: U.S. Appl. No. 10/922,054, dated Mar. 14, 2007, 14 pages.
In the U.S. Patent and Trademark Office, Office Action in re: U.S. Appl. No. 10/922,054, dated Sep. 7, 2006, 21 pages.
In the U.S. Patent and Trademark Office, Restriction Requirement in re: U.S. Appl. No. 10/922,054, dated May 17, 2006, 5 pages.
In the U.S. Patent and Trademark Office, Notice of Allowance and Examiner's Interview Summary in re: U.S. Appl. No. 12/076,062, dated Nov. 2, 2011, 8 pages.
In the U.S. Patent and Trademark Office, Office Action in re: U.S. Appl. No. 12/076,062, dated Jan. 13, 2011, 14 pages.
In the U.S. Patent and Trademark Office, Office Action in re: U.S. Appl. No. 12/355,753, dated Sep. 28, 2011, 32 pages.
In the U.S. Patent and Trademark Office, Ex Parte Quayle Office Action in re: U.S. Appl. No. 29/388,700, dated Oct. 7, 2011, 5 pages.
"AARC Clinical Practice Guideline: Oxygen Therapy in the Home or Extended Care Facility," *Resp. Care*, 1992: 37(8), pp. 918-922.
"ATS Statement: Guidelines for the Six-Minute Walk Test," *Am. J. Respir. Crit. Care Med.*, 2002: 166, pp. 111-117.
"Passy-Muir Speaking Valves," *Respiratory*, Nov. 13, 1998, 7 pages.
Ambrosino, "Exercise and noninvasive ventilatory support," *Monaldi Arch Chest Dis.*, 2000: 55(3): 242-246.
Ambrosino, "Weaning and Respiratory Muscle Dysfunction: The Egg Chicken Dilemma," *Chest*, 2005: 128(2), pp. 481-483.
Bach et al., "Intermittent Positive Pressure Ventilation via Nasal Access in the Management of Respiratory Insufficiency," *Chest*, 1987: 92(1), pp. 168-170.
Banner et al., "Extubating at a Pressure Support Ventilation Level Corresponding to Zero Imposed Work of Breathing," *Anesthesiology*, Sep. 1994: 81(3A), p. A271.
Banner et al., "Imposed Work of Breathing and Methods of Triggering a Demand-Flow, Continuous Positive Airway Pressure System," *Critical Care Medicine*, 1993: 21(2), pp. 183-190.
Banner et al., "Site of Pressure Measurement During Spontaneous Breathing with Continuous Positive Airway Pressure: Effect on Calculating Imposed Work of Breathing," *Critical Care Medicine*, 1992: 20(4), pp. 528-533.
Barakat et al., "Effect of noninvasive ventilatory support during exercise of a program in pulmonary rehabilitation in patients with COPD," *Int. J. Chron. Obstruct. Pulmon. Dis.*, 2007: 2(4), pp. 585-591.
Barreiro et al., "Noninvasive ventilation," *Crit Care Clin.*, 2007; 23(2): 201-22.
Bauer et al., "ADAM Nasal CPAP Circuit Adaptation: A Case Report," *Sleep*, 1991: 14(3), pp. 272-273.
Blanch, "Clinical Studies of Tracheal Gas Insufflation," *Resp. Care*, 2001: 45(2), pp. 158-166.
Borghi-Silva et al., "Non-invasive ventilation improves peripheral oxygen saturation and reduces fatigability of quadriceps in patients with COPD," *Respirology*, 2009, 14:537-546.
Bossi et al., "Continuous Positive Airway Pressure in the Spontaneously Breathing Newborn by Means of Bilateral Nasal Cannulation," *Monatsschr Kinderheilkd*, 1975: 123(4), pp. 141-146.
Boussarsar et al., "Relationship between ventilatory settings and barotrauma in the acute respiratory distress syndrome," *Intensive Care Med.*, 2002: 28(4): 406-13.
Chang et al., "Reduced Inspiratory Muscle Endurance Following Successful Weaning From Prolonged Mechanical Ventilation," *Chest*, 2005: 128(2), pp. 553-559.
Charlotte Regional Medical Center, "Application of the Passy-Muir Tracheostomy and Ventilator," *Speech-Language Pathology Department*, Jan. 1995, 8 pages.
Christopher et al., "Preliminary Observations of Transtracheal Augmented Ventilation for Chronic Severe Respiratory Disease," *Resp. Care*, 2001: 46(1), pp. 15-25.
Christopher, et al., "Transtracheal Oxygen Therapy for Refractory Hypoxemia," *JAMA*, 1986: 256(4), pp. 494-497.
Ciccolella et al.; "Administration of High-Flow, Vapor-phased, Humidified Nasal Cannula Air (HF-HNC) Decreases Work of Breathing (WOB) in Healthy Subjects During Exercise," *AmJRCCM*, Apr. 2001: 163(5), Part 2, pp. A622. (Abstract Only).
Clini et al., "The Italian multicentre study on noninvasive ventilation in chronic obstructive pulmonary disease patients," *Eur. Respir. J.*, 2002, 20(3): 529-538.
Costa et al., "Influence of noninvasive ventilation by BiPAP® on exercise tolerance and respiratory muscle strength in chronic obstructive pulmonary disease patients (COPD)," *Rev. Lat. Am. Enfermagem.*, 2006: 14(3), pp. 378-382.
Díaz et al., "Breathing Pattern and Gas Exchange at Peak Exercise in COPD Patients With and Without Tidal Flow Limitation at Rest," *European Respiratory Journal*, 2001: 17, pp. 1120-1127.
Enright, "The six-minute walk test," *Resp. Care*, 2003: 8, pp. 783-785.
Ferreira et al., "Trigger Performance of Mid-level ICU Mechanical Ventilators During Assisted Ventilation: A Bench Study," *Intensive Care Medicine*, 2008,34:1669-1675.
Fink, "Helium-Oxygen: An Old Therapy Creates New Interest," *J. Resp. Care. Pract. now RT for Decision Makers in Respiratory Care*, 1999, pp. 71-76.
Gaughan et al., "A Comparison in a Lung Model of Low- and High-Flow Regulators for Transtracheal Jet Ventilation," *Anesthesiology*, 1992: 77(1), pp. 189-199.
Gregoretti, et al., "Transtracheal Open Ventilation in Acute Respiratory Failure Secondary to Severe Chronic Obstructive Pulmonary Disease Exacerbation," *Am. J. Resp. Crit. Care. Med.*, 2006: 173(8), pp. 877-881.
Haenel et al., "Efficacy of Selective Intrabronchial Air Insufflation in Acute Lobar Colapse," *Am. J. Surg.*, 1992: 164(5), pp. 501-505.
Keilty et al., "Effect of inspiratory pressure support on exercise tolerance and breathlessness in patients with severe stable chronic obstructive pulmonary disease," *Thorax*, 1994, 49(10): 990-994.
Köhnlein et al., "Noninvasive ventilation in pulmonary rehabilitation of COPD patients," *Respir. Med.*, 2009, 103: 1329-1336.
Koska et al., "Evaluation of a Fiberoptic System for Airway Pressure Monitoring," *J. Clin. Monit.*, 1993: 10(4), pp. 247-250.
Lewis, "Breathless No More, Defeating Adult Sleep Apnea," *FDA Consumer Magazine*, Jun. 1992, pp. 33-37.
Limberg et al., "Changes in Supplemental Oxygen Prescription in Pulmonary Rehabilitation," *Resp. Care*, 2006:51(11), p. 1302.

(56) References Cited

OTHER PUBLICATIONS

Macinryre, "Long-Term Oxygen Therapy: Conference Summary," *Resp. Care*, 2000: 45(2), pp. 237-245.
Macintyre et al., "Acute exacerbations and repiratory failure in chronic obstructive pulmonary disease," *Proc. Am. Thorac. Soc.*, 2008: 5(4), pp. 530-535.
Massie et al., "Clinical Outcomes Related to Interface Type in Patients With Obstructive Sleep Apnea/Hypopnea Syndrome Who Are Using Continuous Positive Airway Pressure," *Chest*, 2003: 123(4), pp. 1112-1118.
Mccoy, "Oxygen Conservation Techniques and Devices," *Resp. Care*, 2000: 45(1), pp. 95-104.
Mcginley, "A nasal cannula can be used to treat obstructive sleep apnea"; *Am. J. Resp. Crit. Care Med.*, 2007: 176(2), pp. 194-200.
Menadue et al., "Non-invasive ventilation during arm exercise and ground walking in patients with chronic hypercapnic respiratory failure," *Respirology*, 2009, 14(2): 251-259.
Menon et al., "Tracheal Perforation. A Complication Associated with Transtracheal Oxygen Therapy," *Chest*, 1993: 104(2), pp. 636-637.
Messinger et al., "Tracheal Pressure Triggering a Demand-Flow CPAP System Decreases Work of Breathing," Anesthesiology, 1994: 81(3A), p. A272.
Messinger et al., "Using Tracheal Pressure to Trigger the Ventilator and Control Airway Pressure During Continuous Positive Airway Pressure Decreases Work of Breathing," *Chest*, 1995: vol. 108(2), pp. 509-514.
Mettey, "Use of CPAP Nasal Cannula for Aids of the Newborns in Tropical Countries," *Medecine Tropicale*, 1985: 45(1), pp. 87-90.
Nahmias et al., "Treatment of the Obstructive Sleep Apnea Syndrome Using a Nasopharyngeal Tube", *Chest*, 1988:94(6), pp. 1142-1147.
Nava et al., "Non-invasive ventilation," *Minerva Anestesiol.*, 2009: 75(1-2), pp. 31-36.
Passy-Muir Inc., "Clinical Inservice Outline", Apr. 2004, 19 pages.
Peters et al., "Combined Physiological Effects of Bronchodilators and Hyperoxia on Exertional Dyspnea in Normoxic COPD," *Thorax*, 2006: 61, pp. 559-567.
Polkeyet al., "Inspiratory pressure support reduces slowing of inspiratory muscle relations rate during exhaustive treadmill walking in sever COPD," *Am. J. Resp. Crit. Care Med.*, 1996: 154(4, 10), pp. 1146-1150.
Porta et al., "Mask proportional assist vs pressure support ventilation in patients in clinically stable condition with chronic venilatory failure," *Chest*, 2002: 122(2), pp. 479-488.
Prigent et al., "Comparative Effects of Two Ventilatory Modes on Speech in Tracheostomized Patients with Neuromuscular Disease," *Am. J. Resp. Crit. Care Med.*, 2003: 167(8), pp. 114-119.
Puente-Maestu et al., "Dyspnea, Ventilatory Pattern, and Changes in Dynamic Hyperinflation Related to the Intensity of Constant Work Rate Exercise in COPD," *Chest*, 2005: 128(2), pp. 651-656.
Ram et al., "Non-invasive positive pressure ventilation for treatment of respiratory failure due to exacerbations of chroic obstructive pulmonary disease," *Cochrane Database Syst Rev.*, 2004(3):1-72.
Rothe et al., "Near Fatal Complication of Transtracheal Oxygen Therapy with the SCOOP(R) System," *Pneumologie*, 1996: 50(10), pp. 700-702. (English Abstract provided.).
Rothfleisch et al., "Facilitation of fiberoptic nasotracheal intubation in a morbidly obese patient by simultaneous use of nasal CPAP," Chest, 1994, 106(1): 287-288.
Sanders et al., "CPAP Via Nasal Mask: A Treatment for Occlusive Sleep Apnea," *Chest*, 1983: 83(1), pp. 144-145.
Sinderby et al., "Neural control of mechanical ventilation in respiratory failure," *Nat. Med.*, 1999: 5(12), pp. 1433-1436.
Somfay et al., "Dose-Response Effect of Oxygen on Hyperinflation and Exercise Endurance in Nonhypoxaemic COPD Patients," *Eur. Resp. J.*, 2001: 18, pp. 77-84.
Sullivan et al., "Reversal of Obstructive Sleep Apnoea by Continuous Positive Airway Pressure Applied Through the Nares," *The Lancet*, 1981: 1(8225), pp. 862-865.

Sullivan, "Home treatment of obstructive sleep apnoea with continuous positive airway pressure applied through a nose-mask," *Bull Eur Physiopathol Respir.*, 1984: 20(1), pp. 49-54.
Tiep et al., "Pulsed nasal and transtracheal oxygen delivery," *Chest*, 1990: 97, pp. 364-368.
Tsuboi et al., "Ventilatory Support During Exercise in Patients With Pulmonary Tuberculosis Sequelae," *Chest*, 1997: 112(4), pp. 1000-1007.
*VJA/DOD Clinical Practice Guideline*, "Management of Chronic Obstructive Pulmonary Disease," Aug. 1999, Ver. 1.1a, Updated Nov. 1999.
Wijkstra et al., "Nocturnal non-invasive positive pressure ventilation for stable chronic obstructive pulmonary disease," *Cochrane Database Syst. Rev.*, 2002, 3: 1-22.
Yaeger et al., "Oxygen Therapy Using Pulse and Continuous Flow With a Transtracheal Catheter and a Nasal Cannula," *Chest*, 1994: 106, pp. 854-860.
Walsh, "McGraw Hill Pocket reference Machinists' and Metalworker Pocket Reference," *New York McGraw-Hill*, 2000, pp. 3-67, submitting 3 pages.
International Preliminary Report and Written Opinion on Patentability for PCT/DE2004/001646, dated Jul. 3, 2006.
European patent Office Search Report dated Oct. 19, 2007 in co-pending EP 04762494.
International Search Report and Written Opinion for PCT/US04/26800 dated Jun. 22, 2006.
International Search Report and Written Opinion for PCT/US07/12108, dated Aug. 8, 2008.
International Search Report and Written Opinion for PCT/US07/17400, dated Apr. 28, 2008.
International Search Report and Written Opinion for PCT/US08/64015, dated Sep. 26, 2008.
International Search Report and Written Opinion for PCT/US08/64164, dated Sep. 29, 2008.
International Search Report and Written Opinion for PCT/US08/78031, dated Nov. 24, 2008.
International Search Report and Written Opinion for PCT/US08/78033, dated Dec. 3, 2008.
International Search Report and Written Opinion for PCT/US09/054673, dated Oct. 8, 2009.
International Search Report and Written Opinion for PCT/US09/41027, dated Dec. 14, 2009.
International Search Report and Written Opinion for PCT/US09/59272, dated Dec. 2, 2009.
International Search Report and Written Opinion for PCT/US2006/036600, dated Apr. 3, 2007.
International Search Report and Written Opinion for PCT/US2009/031355 dated Mar. 11, 2009.
International Search Report and Written Opinion for PCT/US2009/041034, dated Jun. 10, 2009.
International Search Report and Written Opinion for PCT/US2010/029871, dated Jul. 12, 2010.
International Search Report and Written Opinion for PCT/US2010/029873, dated Jun. 28, 2010.
International Search Report and Written Opinion for PCT/US2010/029874, dated Jul. 12, 2010.
International Search Report and Written Opinion for PCT/US2010/029875, dated Jul. 12, 2010.
International Search Report and Written Opinion for PCT/US2010/047920, dated Nov. 1, 2010.
International Search Report and Written Opinion for PCT/US2010/047921, dated Jan. 27, 2011.
International Search Report for PCT/DE2004/001646, dated Jan. 17, 2005.
State Intellectual Property Office of P.R.C., Notification of the First Office Action, dated Sep. 25, 2014, 3 Pages.
State Intellectual Property Office of P.R.C., Search Report for Application No. 201180039491.5, 2 Pages, dated Sep. 25, 2014.
English Translation of Japanese Office Action for Japanese Application No. 2013-524940. dated Jun. 2, 2015.
Extended European Search Report for EP11818693.1; dated Jun. 15, 2016.

(56) References Cited

OTHER PUBLICATIONS

Patent Examination Report, dated Apr. 3, 2014, 4 Pages, Melbourne Australia.
Canadian Office Action for CA 2,807,416; dated Apr. 12, 2018.

* cited by examiner

METHODS, SYSTEMS AND DEVICES USING LOX TO PROVIDE VENTILATORY SUPPORT

CROSS-REFERENCE TO RELATED APPLICATIONS

This application claims priority to U.S. Provisional Patent Application No. 61/374,126, filed Aug. 16, 2010; the content of which is incorporated herein by reference in its entirety.

FIELD OF THE INVENTION

The present invention relates to ventilation therapy for persons suffering from respiratory and breathing disorders, such as respiratory insufficiency and sleep apnea. More specifically, the present invention relates to methods and apparatus for assisting in the work of breathing, and restoring, augmenting, or providing ventilation to the lungs using a liquid oxygen (LOX) supply as a gas source.

BACKGROUND OF THE INVENTION

There are a range of clinical syndromes that require some form of mechanical ventilation therapy with elevated concentrations of inspired oxygen. These syndromes include hypoxemia, various forms of respiratory insufficiency, and congestive heart failure. Ventilators that treat these conditions provide ventilatory support for the lung, and typically deliver elevated concentrations of oxygen to help oxygenate the organs. The oxygen supplies used as inputs to these ventilators are typically compressed oxygen gas in cylinders or a hospital's compressed oxygen supply piped into the treatment room. More recently, attempts have been made to tee oxygen into a ventilator from an oxygen concentrator, which makes 92% oxygen from room air. In general, even the most portable ventilation therapy systems have limited portability due to the size and weight of the ventilator. Additionally, if the patient requires elevated concentrations of oxygen, also because of the size and weight of the oxygen cylinder that is required as input to the ventilator. Because of this, a large number of patients that need ventilatory support choose not to have it because they do not want to be immobilized by being connected to a conventional ventilator. To solve this dire unmet need, recently, a unique new ventilation system has been devised (U.S. Pat. Nos. 7,487,778, 7,533,670 and 7,588,033) that works using non-conventional gas delivery and patient interface principles, which render the ventilation and oxygen supply equipment highly portable, and in fact wearable. Thus, for the first time, patients that require mechanical ventilatory support can have that support while conveniently and easily ambulating.

Separate from mechanical ventilation therapy, there are also clinical syndromes that require oxygen therapy, but not necessarily ventilatory support. These oxygen therapy systems include compressed oxygen gas in cylinders, oxygen concentrators, and liquid oxygen (LOX) systems. These liquid oxygen systems store oxygen in liquid form, and over time the liquid oxygen converts to gaseous oxygen before being delivered to the patient as gaseous oxygen. LOX can be very advantageous in that it has a more efficient gas volume to storage volume ratio. A liter of LOX typically creates about 800 liters of gaseous oxygen at atmospheric pressure, whereas one liter of compressed oxygen gas in a cylinder typically creates about 100 liters of gaseous oxygen at atmospheric pressure.

In the ambulatory mechanical ventilatory support system described in U.S. Publication Nos. 2008/0135044, 2010/0252042, 2010/0252041, 2010/0252040, 2010/0252039, 2010/0252037, use of LOX has been described for (A) an oxygen supply for a mechanical ventilator, and (B) to use the gas pressure created by a LOX system to power a pneumatically powered ventilator. The advantage of using LOX as an input to a mechanical ventilator is that it can help make the ventilation system highly portable, which is very useful in many clinical applications such as chronic obstructive pulmonary disease (COPD), interstitial lung disease (ILD), some neuromuscular diseases, as well as field and pandemic uses. However, to be technically feasible to use a LOX system for the input into such a ventilator, the LOX system, the ventilator, or both, requires special unique features.

In summary, existing mechanical ventilation therapies have the following disadvantages: they do not offer respiratory support in an ambulatory form factor that can be easily borne or worn by the patient.

SUMMARY OF THE INVENTION

The present invention solves the limitations of prior systems with unique features that allow use of a ventilator in conjunction with LOX. Embodiments of the present invention include a portable liquid oxygen system providing an average flow rate of oxygen gas at approximately 6-approximately 20 lpm using a rapid gas conversion mode. The liquid oxygen system may weigh less than 10 pounds. A heat exchanger may be provided, and wherein the rapid gas conversion mode may utilize a heater on the heat exchanger. The rapid gas conversion mode may utilize a Stirling engine passing air from a heat source across the heat exchanger to a heat sink, wherein the heat source is ambient air, and wherein the heat sink is proximal to a liquid oxygen store. A liquid oxygen store may be provided, and wherein the rapid gas conversion mode may utilize a reduction in insulation at least partially surrounding the liquid oxygen store. An oxygen gas store may be provided, and wherein higher peak flow rates than the average flow rate may be achieved utilizing oxygen stored in the oxygen gas store. The system may have multiple modes of operation. The modes of operation may be a continuum of settings and not discrete modes of operation. Flow capacity may be changed when switching between modes of operation. Oxygen gas pressure may be changed when switching between modes of operation. The system may automatically switch modes of operation based on a patient's condition.

Embodiments of the present invention may also include a ventilation system that includes a portable ventilator; and a portable liquid oxygen system providing a flow rate of oxygen gas at approximately 6-approximately 20 lpm using a rapid gas conversion mode. The portable ventilator and the portable liquid oxygen system may be integrated into a single portable or wearable unit. The liquid oxygen system may weigh less than 10 pounds. A heat exchanger may be provided, and wherein the rapid gas conversion mode may utilize a heater on the heat exchanger. The rapid gas conversion mode may utilize a Stirling engine passing air from a heat source across the heat exchanger to a heat sink, wherein the heat source is ambient air, and wherein the heat sink is proximal to a liquid oxygen storage device. A liquid oxygen storage device may be provided, and wherein the rapid gas conversion mode may utilize a reduction in insulation at least partially surrounding the liquid oxygen storage device. An oxygen gas store may be provided, and wherein peak flow requirements of the portable ventilator may be achieved by utilizing oxygen stored in the oxygen gas store. A patient interface may be provided, wherein the patient interface is a nasal interface, a mask, an endotracheal tube, a tracheostomy tube, or a trans-oral tube. The ventilator may be wearable. A blender may be provided for titrating the amount of oxygen needed.

Embodiments of the present invention may include a liquid oxygen system including a liquid oxygen store; a heat exchanger; a fan; a heat source; and a heat sink, wherein the fan passes ambient air across the heat exchanger from the heat source to the heat sink to produce a rapid gas conversion mode. The liquid oxygen system may be portable. The heat source may be an opening to ambient. The heat sink may be a region near the liquid oxygen store or evaporative coils.

Embodiments of the present invention may include a portable liquid oxygen system including a liquid oxygen store; an oxygen gas store; a liquid oxygen to gas conversion unit, wherein the liquid oxygen to gas conversion unit further comprises a heat exchanger between the liquid oxygen store and the oxygen gas store; and one or more controls for determining a mode of operation for the heat exchanger. The mode of operation may be switched automatically. A mode of the heat exchanger may be a rapid gas conversion mode for ventilation therapy providing an average gas flow at approximately 6 lpm to approximately 20 lpm. A mode of the heat exchanger may be a low gas conversion mode for oxygen therapy providing an average gas flow at approximately 1 lpm to approximately 6 lpm. The one or more controls may receive a signal from one or more respiration sensors, and wherein the one or more controls may cause the heat exchanger to switch between modes. The one or more controls may receive a signal from one or more pulse oximeters, and wherein the one or more controls may cause the heat exchanger to switch between modes.

Embodiments of the present invention may include a method of treating respiratory and breathing disorders, the method including providing a portable liquid oxygen system, wherein the liquid oxygen system comprises a liquid oxygen store, an oxygen gas store, a liquid oxygen to gas conversion unit, a heat exchanger between the liquid oxygen store and the oxygen gas store; and providing an average flow rate of oxygen gas at approximately 6-approximately 20 lpm using a rapid gas conversion mode. The method may also include receiving an input from one or more respiration sensors regarding ventilation needs of the patient at one or more controls; automatically determining a mode of operation for the heat exchanger based on signals from one or more respiration sensors; and sending a control signal to one or more of the liquid oxygen store, the oxygen gas store, the liquid oxygen to gas conversion unit, and the heat exchanger to initiate the determined mode of operation. The liquid oxygen system may weigh less than 10 pounds. The rapid gas conversion mode may utilize a heater on a heat exchanger. The rapid gas conversion mode may utilize a Stirling engine passing air from a heat source across a heat exchanger to a heat sink, wherein the heat source is ambient air, and wherein the heat sink is proximal to the liquid oxygen storage device. The rapid gas conversion mode may utilize a reduction in insulation at least partially surrounding the liquid oxygen store. Higher peak flow rates than the average flow rate may be achieved utilizing oxygen stored in the oxygen gas store.

Additional features, advantages, and embodiments of the invention are set forth or apparent from consideration of the following detailed description, drawings and claims. Moreover, it is to be understood that both the foregoing summary of the invention and the following detailed description are exemplary and intended to provide further explanation without limiting the scope of the invention as claimed.

BRIEF DESCRIPTIONS OF THE FIGURES

The accompanying drawings, which are included to provide a further understanding of the invention and are incorporated in and constitute a part of this specification, illustrate preferred embodiments of the invention and together with the detailed description serve to explain the principles of the invention. In the drawings.

DETAILED DESCRIPTION OF THE EMBODIMENTS

Figure 1:
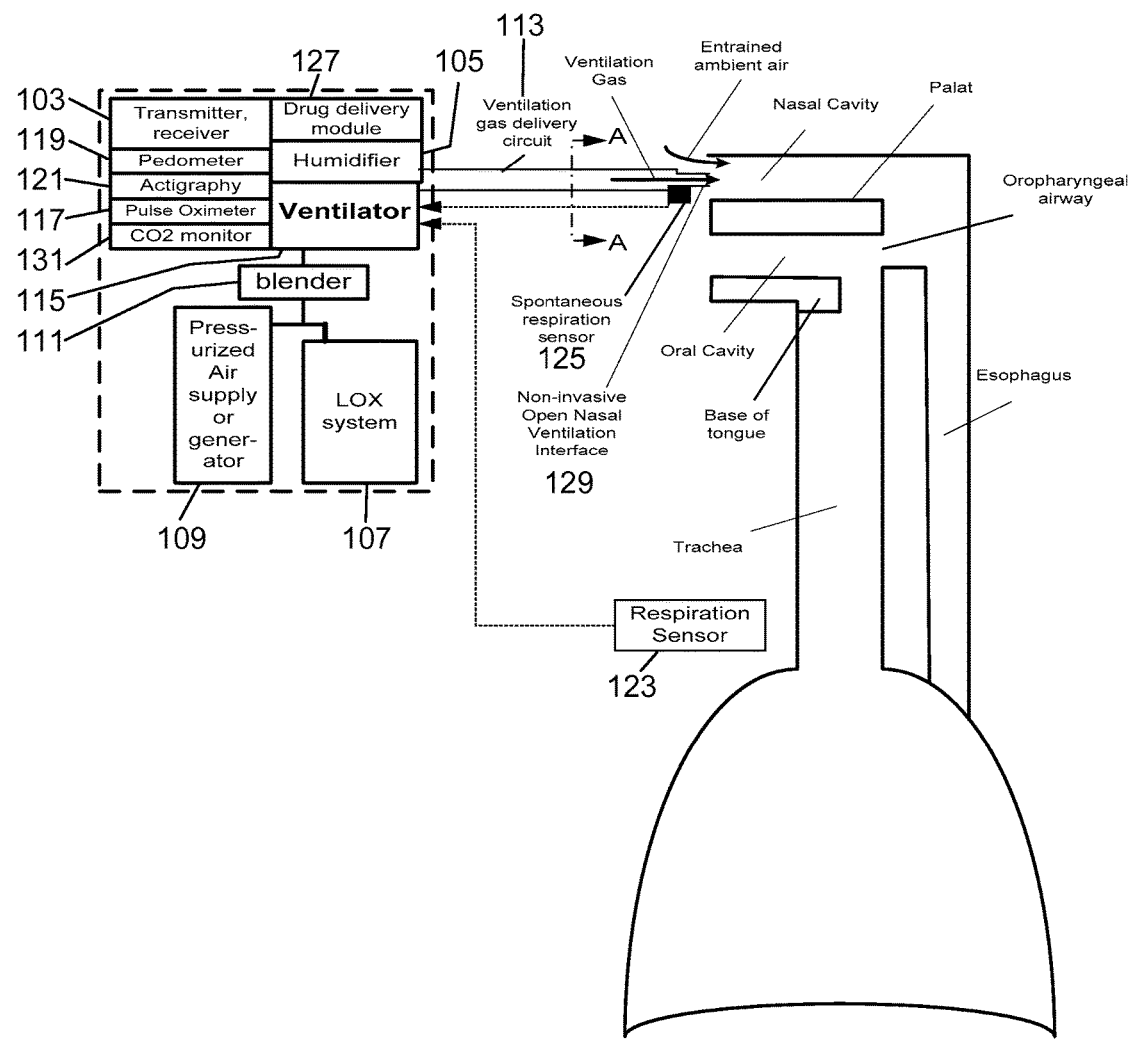
FIG. 1 is a system schematic of the invention, according to an exemplary embodiment.

The present invention may include LOX systems that are used for (A) input to a ventilator for the ventilator to deliver elevated concentrations of oxygen to the patient, and (B) for providing pressurized gas input to a ventilator to drive the ventilator with pneumatic power. The latter may allow the ventilator to consume relatively small amounts of electrical power, thus enabling the ventilator to be portable using battery power for extended periods.

The present invention may provide ventilation to a patient using a ventilation system that typically employs a non-invasive nasal interface or a transtracheal interface. The present invention can be used to treat respiratory insufficiency by providing mechanical ventilation to support the work of breathing of a patient. The patient interface may include a jet pump having a geometric configuration that optimizes the fluid dynamics of the system to improve the efficiency of the system and efficacy of the therapy. A pressurized gas, such as a therapeutic gas, and more specifically oxygen-rich gas, may be delivered through a catheter. For purposes of this disclosure, the terms tube, catheter, hose, gas delivery circuit, etc. are used interchangeably. Further, the term catheter does not necessarily require insertion into a patient airway, and does not require the device to be long and flexible. Various configurations are possible depending on specific uses. When the pressurized gas exits a catheter distal tip, the gas may entrain approximately 25-250% of ambient air due to the design of the catheter, so that a combination of ventilator-delivered gas and entrained gas is delivered to the patient. Embodiments of the present invention may, for example, create an increase of approximately 2-40 cmH$_2$O in the upper airway, and approximately 1-30 cmH$_2$O in the lung. A ventilator-delivered gas volume of approximately 50 ml can entrain for example approximately 50 ml, so that approximately 100 ml is delivered to the patient, with a sufficient driving pressure so that a significant amount of the approximately 100 ml volume reaches the airway or lung to increase pressure in those areas, thus mechanically supporting respiration. For purposes of this disclosure, nasal cannula, nasal catheter, jet nozzle, and ventilation interface are often used interchangeably when pertaining to the present invention. Other ventilation interfaces can also be used, such as conventional non-invasive ventilation masks or airway tubes, etc.

Embodiments of the present invention may provide ventilation to a patient using a ventilator described as follows. The ventilator can be wearable, and weight less than approximately 3 lbs, preferably approximately 1 lb. The ventilator typically includes a valve that regulates the output of the ventilator to a desired volume, pressure or flow. The ventilator typically includes other features related to patient activity, such as actigraphy or pedometry sensing, biofeedback control of the therapy level based on patient's activity level, dyspnea questionnaires, and bi-directional communication capability with a remote clinician. The ventilator can also include a piston or reservoir system for amplifying the output pressure or storing oxygen gas volume in-between volume deliveries to the patient.

FIG. 1 is a schematic diagram showing an exemplary overall system of the invention. A patient may be ventilated using a ventilation gas delivery circuit 113 and non-invasive open nasal ventilation interface 129, or other interfaces, such as endotracheal tubes, trans-oral tubes, etc. The nasal interface 129 preferably does not seal against the patient's nose, and instead leaves the nose open for the user to breathe normally and freely from the ambient surroundings. Ventilation gas may be delivered at a speed that entrains ambient air, such that the combination of ventilation gas and entrained air are delivered to the user's airways and lung under power. The nasal interface 129 may optimize the physics and fluid dynamics to maximize its performance.

The ventilation system may include several primary components: (1) a LOX storage portion, (2) a LOX gas conversion and storage portion, (3) an oxygen gas storage portion, (4) a ventilator portion, (5) a gas delivery circuit, and (6) a patient interface or mask. The LOX storage, LOX gas conversion and storage, the oxygen gas storage portion, and the ventilator can be separate units or can be integrated into one unit or more units. A spontaneous breathing respiration sensor may also be used to detect, determine and measure the spontaneous breathing pattern/phases of the user. This information may be used to synchronize and/or titrate the therapy to the needs of the patient and to match the gas delivery comfortably with the patient's breathing.

Embodiments of the present invention may be used to support the respiration of the patient, including supporting the work of breathing by increasing pressure and volume in the lung. When using the invention, the patient breathes normally through their upper airway and through their nose, while receiving mechanical support through the interface. The patient can keep their mouth closed during use, to help direct the mechanical support to the lower airways, or can use a bite block or mouth guard or chin band, if necessary. The patient can use the therapy while stationary, while being transported, while mobile and active, or while resting or sleeping. The therapy has homecare, hospital, subacute care, emergency, military, pandemic and transport applications. It should be noted that the LOX storage and LOX gas conversion aspects of the invention can be used to supply ventilation gas to conventional ventilators or for conventional oxygen therapy delivery systems, and other medical and non-medical applications, in addition to delivering oxygen to the ambulatory non-invasive open airway ventilation system.

Figure 2:
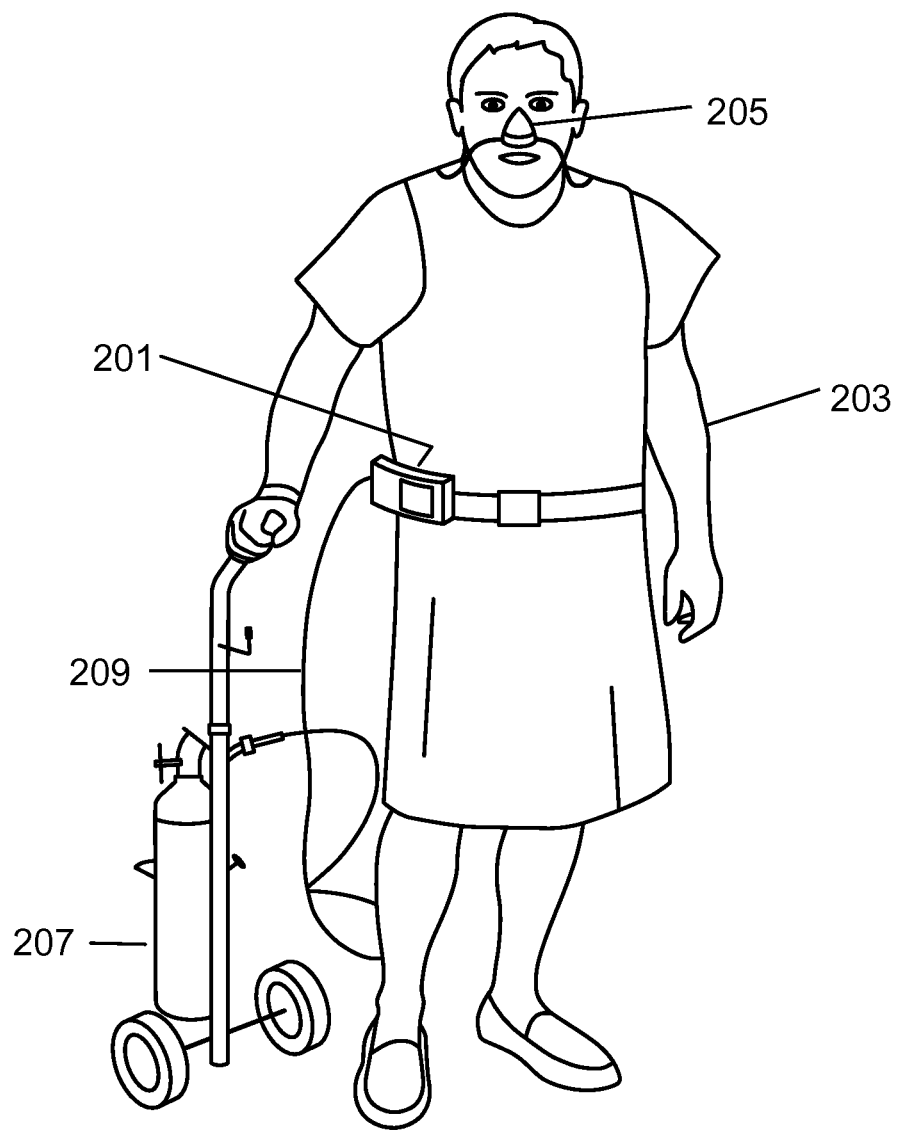
FIG. 2 illustrates a patient using an exemplary embodiment of the present invention for treating respiratory insufficiency.

FIG. 2 shows an exemplary embodiment as used to treat respiratory insufficiency. A ventilator 201 can be borne or worn by the patient 203, such as being placed discretely on the user's body, head or face. Because the ventilation system may contribute to some of the mechanical work required for a person to breathe, the user can be active without suffering from dyspnea, hypoxemia, hypercapnia or fatigue. The user can benefit from ambulation, activity, and participate in the routine activities of daily living, such as preparing meals, bathing, chores around the house, and leaving the house for outside activities. Further, the user can communicate, eat, drink and swallow, while receiving mechanical ventilation, as opposed to other ventilation interfaces in which the patient's airway is closed with an external mask, or sealed internally with a cuffed airway tube. The ventilation parameters, ventilation timing algorithms, and the effect on the lung are described in subsequent descriptions. The patient 203 may breathe through an interface 205, such as a nasal interface. The ventilator 201 may be coupled to an external oxygen supply 207 via conduits 209.

Figure 3:
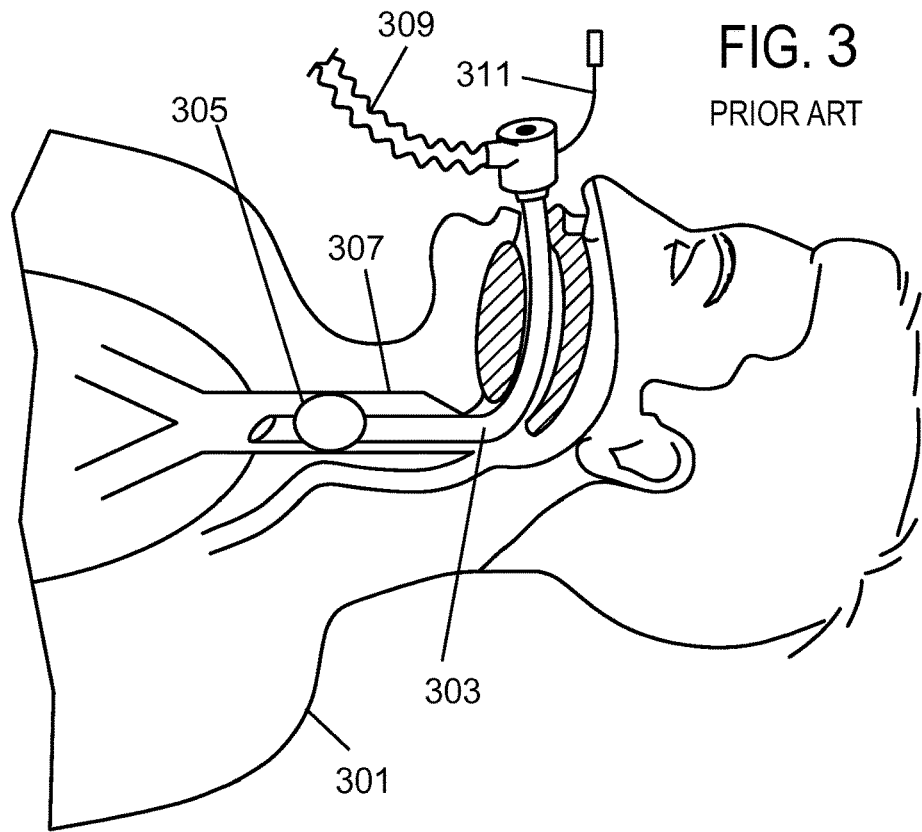
FIG. 3 illustrates prior art controlled mechanical ventilation.

FIG. 3 shows a prior art therapy for mechanical ventilation. A patient 301 is intubated with an endotracheal (ET) tube 303 and a cuff 305 is inflated in the trachea 307, thus closing the airway off from ambient air. The patient 301 is sedated and their lungs are ventilated with gas being delivered and removed through the ET tube 303. Gas may be delivered through a gas delivery tube 309. A sensor 311 may measure airflow. This therapy is highly effective in providing mechanical support for respiration; however, in some situations such as field emergencies, providing elevated concentrations of oxygen gas may be required.

Figure 4:
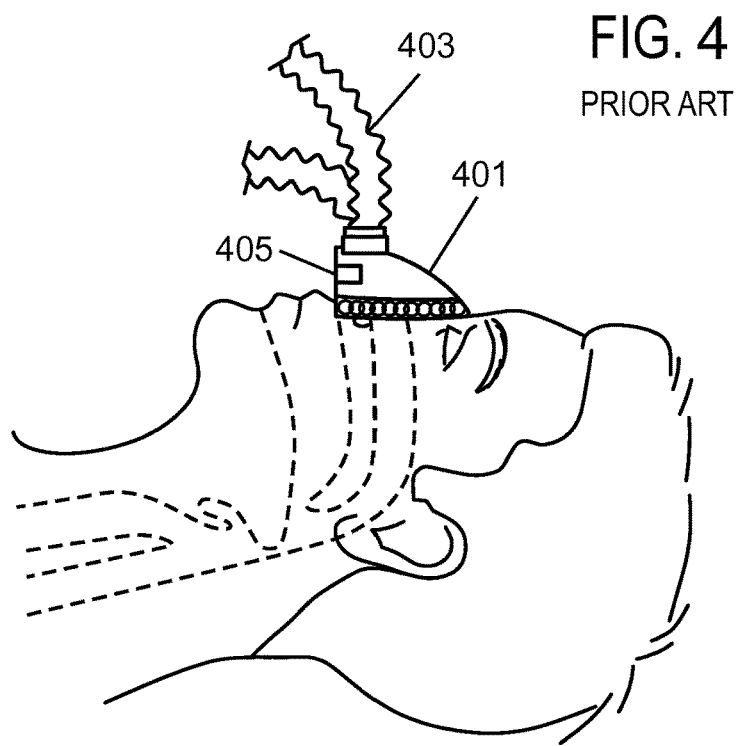
FIG. 4 illustrates prior art continuous positive airway pressure (CPAP) ventilation.

FIG. 4 shows a prior art respiratory support therapy, non-invasive ventilation, using a nose mask 401 and typically using a BiPAP ventilation mode. Non-invasive ventilation (NIV) is used to breathe for the patient, or can be used to help the breathing of a patient, in which case the patient's spontaneous breathing effort triggers the ventilator to deliver the pressure or volume based mechanical ventilation. All of the volume delivered to and from the lungs is delivered and removed from a ventilation circuit 403 and the nose mask 401. A similar system can be used for obstructive sleep apnea, in which case exhaust vents 405 are included in the nose mask so that a portion of the exhaled gas is exhaled through the vent ports. NIV, CPAP and bilevel positive airway pressure (BiPAP) are clinically very effective for spontaneously breathing patients; however, these modes and therapies do not facilitate activities of daily living, the ventilator can not be borne by the patient, the patient cannot breathe room air naturally and freely, and the patient's upper airway cannot function normally and naturally because it is sealed off with the external mask seal.

Figure 5:
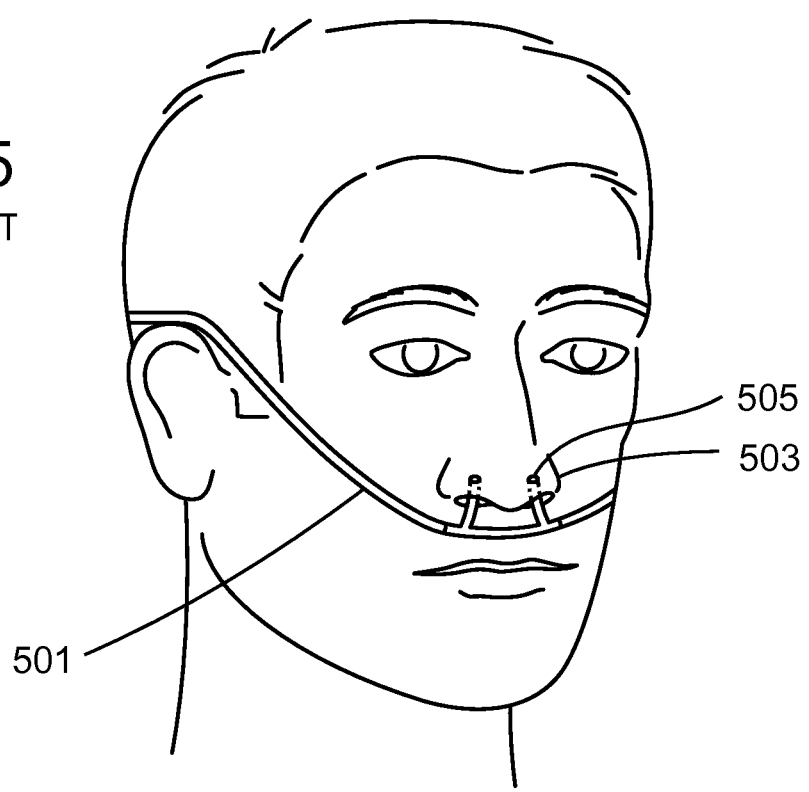
FIG. 5 illustrates prior art nasal cannula oxygen therapy.

FIG. 5 shows the conventional prior art oxygen delivery cannula 501, for administering oxygen therapy. Distal ends of the cannula 505 are configured to enter the nares 503. The proximal end is connected to an oxygen delivery device that can deliver continuous flow oxygen at 1-6 lpm to the user's nose, or which delivers a bolus of oxygen upon detection of an inspiratory effort. This prior art does not mechanically support the work of breathing of the patient.

Figure 6A:
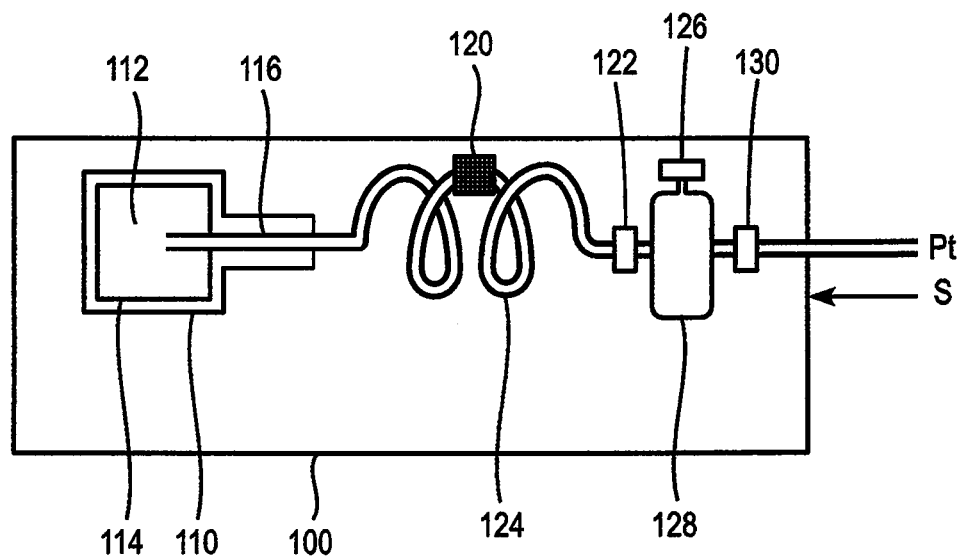
FIG. 6A is a schematic of a LOX system, according to an exemplary embodiment.

In FIG. 6A, a LOX system is described to provide pressure and flow required for a ventilator. Exemplary embodiments may include a ventilator 100, LOX unit 110, LOX 112, LOX unit vacuum chamber 114, LOX outlet tube 116, heat exchanger 124, heater 120, check valve 122, oxygen gas reservoir 128, reservoir pressure regulator 126, gas outlet on/off valve 130, outlet to patient Pt and incoming breath signal S.

Typical LOX systems include a liquid phase oxygen compartment and an oxygen gas phase compartment that is continually filled by the boiling of the liquid oxygen. The phase change is catalyzed by a heat exchanger unit. These systems maintain the gas phase compartment at about 23 psi by bleeding gas to atmosphere to avoid pressurization beyond 23 psi. Typical medical LOX systems have been designed specifically to conserve oxygen and as such their output is relatively weak compared to the requirements of a ventilator. The compact LOX systems that are designed for portability are engineered to deliver gas at very low flow rates (<3 lpm) and low pressures (below 5 psi). The larger, less portable LOX units are engineered for greater flow output; however, these units are not realistically suited for active ambulatory patients because of their larger size. The typical systems are capable of delivering oxygen gas at a continuous flow rate of below 4 lpm at a pressure well below 23 psi since the pressure in the gas phase compartment drops within fractions of a second when the system is opened to the patient. The gas phase compartment typically contains less than 50 ml of gas and the rate of gas creation by boiling is limited to below 4 lpm due to the design and construction of the heat exchanger, which is typically less than 20 square inches surface area. Gas flow output to the patient is also limited by the size of the orifice in the outlet valve, typically less than 0.10" diameter, thus restricting airflow.

In the present invention the heat exchanger unit 124 is designed with greater surface area, typically greater than 30 square inches, to produce gas at the rate of 6-10 lpm and the outlet orifice allows that flow rate output as well, typically greater than 0.15" diameter. The heater 120 may be added to increase the rate of production of gaseous oxygen. The gas volume of the gas phase compartment is typically above approximately 80 ml and can be approximately 250 ml, which typically includes a pressure regulator 126, a reservoir 128, check valve 122, on/off valve 130 and incoming breath signal S. This configuration may provide an oxygen gas output flowrate of above approximately 6 lpm at above approximately 20 psi continuously, thus meeting the parameters required by some ventilators. The LOX system may include a catheter and all the requisite sensing components and timing functions described herein to deliver the required volume of gas at the correct pressure and at the correct time of the breathing curve.

Figure 6B:
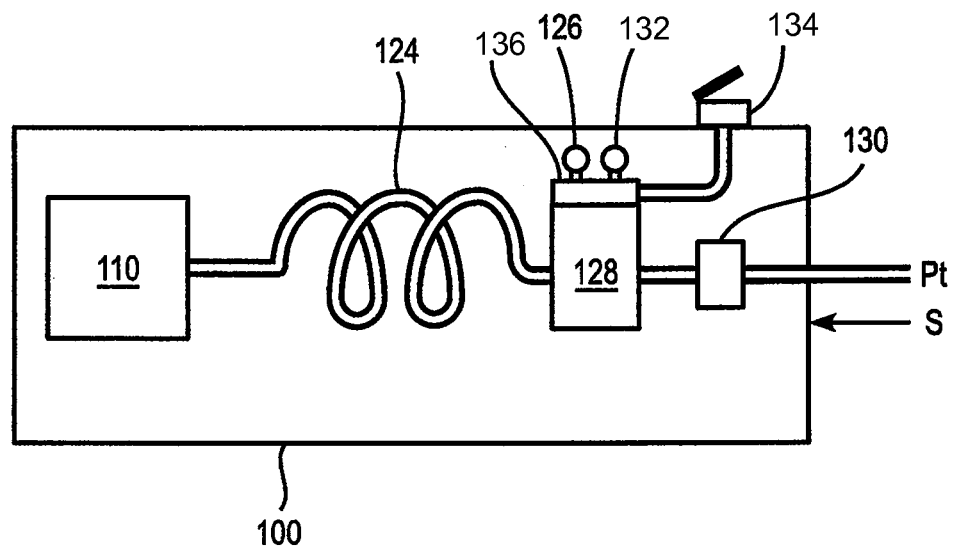
FIG. 6B is a schematic of a two pressure setting LOX system, according to an exemplary embodiment.

An additional embodiment is shown in FIG. 6B, where a LOX system includes two pressure settings. A low pressure regulator 126 with a setting of approximately 23 psi may be used when a patient requires less powerful therapy or needs to conserve the LOX. A higher pressure regulator 132 with a setting of approximately 30-50 psi may be used for increasing the output of the unit when needed or when conserving the LOX is not a concern. For example, when traveling on an airplane, the LOX system can be set at the low 23 psi setting, and reset to the high setting after the flight or when arriving to the destination where there is a refill station. The two pressure regulators may be configured in a manifold 136 that can be operated by a switch 134 to switch between settings. During flight, the patient can still receive the ventilation therapy but at a lower level of augmentation corresponding the to 23 psi setting. After the flight and when the patient becomes more active again, the augmentation level can be increased because the pressure is set to the higher output setting. Two pressure settings are exemplary and it can be any number of pressure settings or even a continuous adjustment of the pressure setting between a minimum and maximum value. The modes of operation of the LOX system may be a continuum of settings and not discrete modes of operation in certain embodiments.

Figure 7:
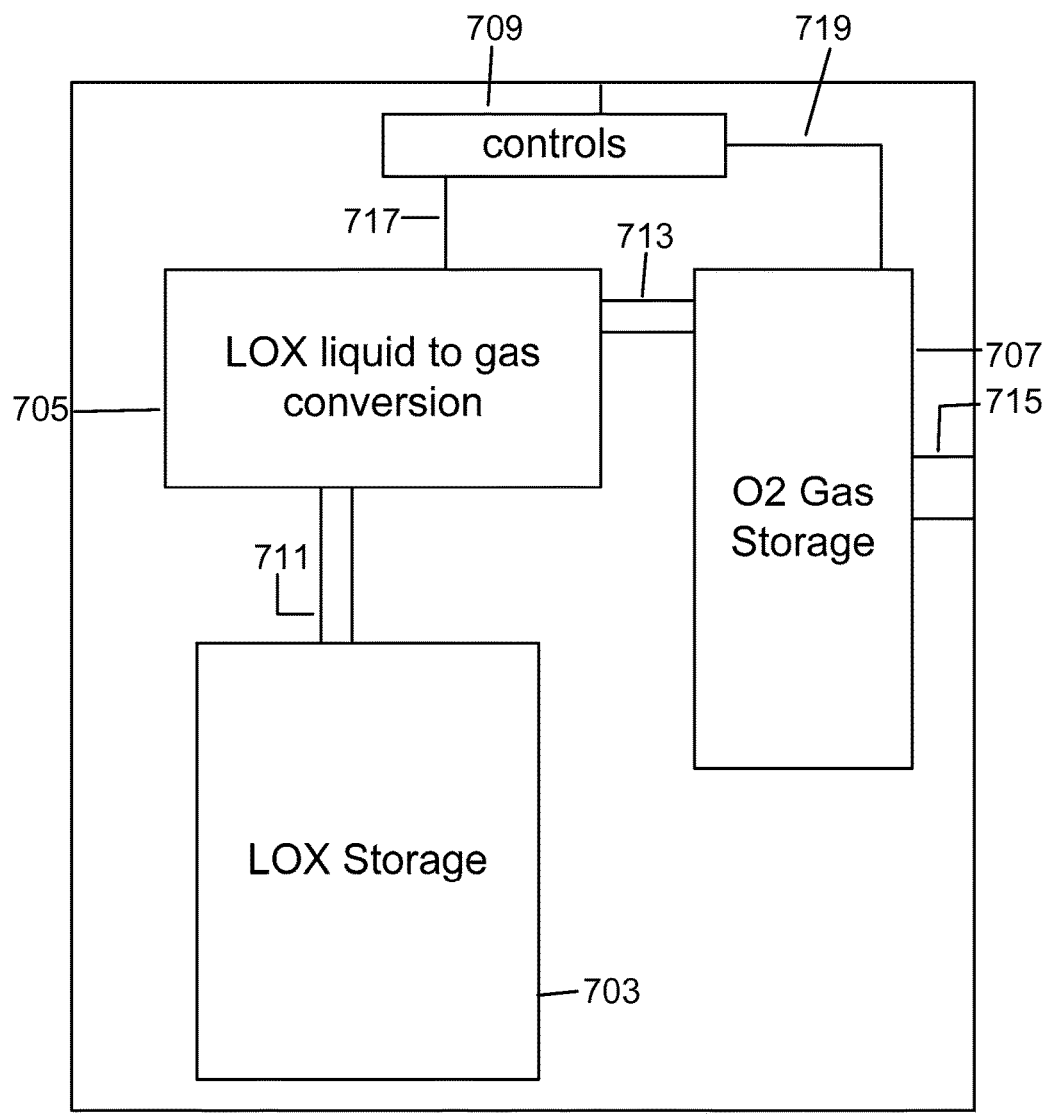
FIG. 7 is a schematic of a LOX module, according to an exemplary embodiment.

FIG. 7 shows an exemplary overall LOX device 701 according to an embodiment of the present invention. Generally, the LOX device 701 may have components including, but not limited to, a LOX storage 703, a LOX liquid to gas conversion device 705, an oxygen gas storage device 707, and one or more controls 707. The LOX storage 703 may be in fluid communication 711 with the LOX liquid to gas conversion device 705. The LOX liquid to gas conversion device 705 may be in fluid communication 713 with the oxygen gas storage device 707. The oxygen gas storage device 707 may be in fluid communication 715 with the exterior of the overall LOX device 701, and other devices such as an oxygen delivery system, a gas delivery circuit, ventilator, etc. The one or more controls 707 may provide control signals 717, 719 to various components internal or external to the LOX device 701. The oxygen gas storage device 707 may be sized appropriately to support the spontaneous oxygen needs of a ventilation system, whereas the LOX liquid to gas conversion device 705 may only be able to support the average oxygen needs of a ventilation system.

The LOX system 701 may be portable and/or wearable. In preferred embodiments, the LOX system may weigh less than 20 lbs, more preferably less than 15 lbs, more preferably less than 10 lbs, and more preferably less than 5 lbs. Weights of the LOX system less than 10 lbs may allow for a patient to comfortable carry and/or wear the device while moving.

Figure 8:
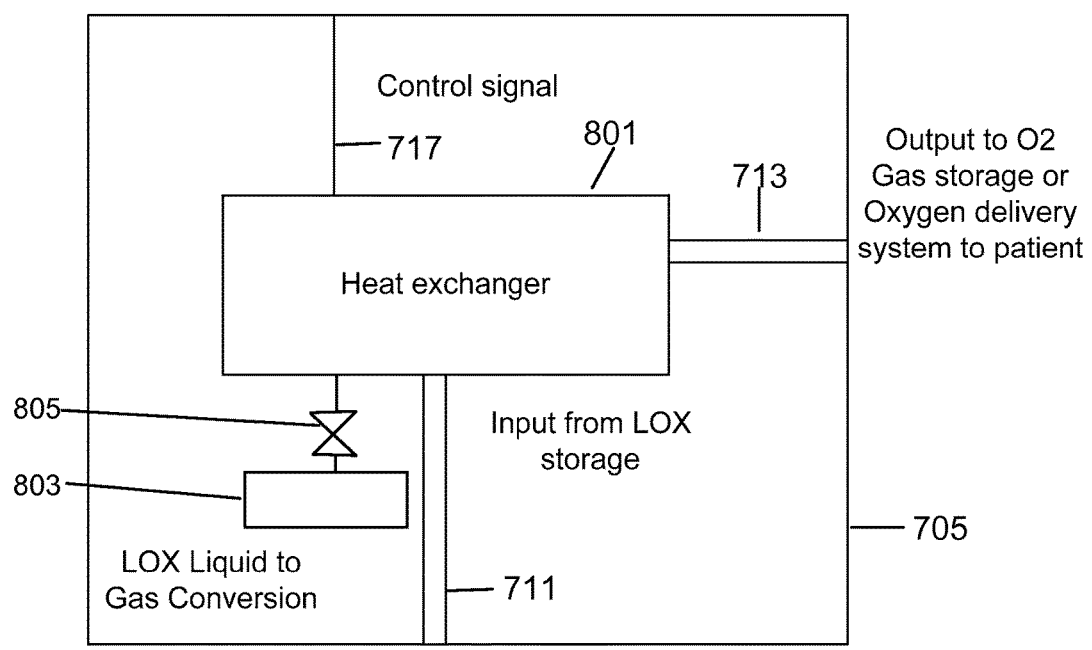
FIG. 8 is a schematic of a LOX gas conversion module, according to an exemplary embodiment.

FIG. 8 shows the LOX liquid to gas conversion device 705 according to one embodiment. The LOX liquid to gas conversion device 705 may typically include a heat exchanger 801 that receives liquid oxygen via the LOX storage 703 via its input 711 and outputs gaseous oxygen to the oxygen gas storage device 707 via its output 713. The heat exchanger 801 may have multiple modes that are controlled via a control signal 717, for instance to switch between low average oxygen gas output flowrates, such as approximately 1 lpm to approximately 6 lpm, preferably approximately 3 lpm, and high average flowrates, such as above approximately 6 lpm, preferably between approximately 6 lpm and approximately 20 lpm. Alternative higher average flowrates may include greater than approximately 7 lpm, greater than approximately 8 lpm, greater than approximately 9 lpm, greater than approximately 10 lpm, greater than approximately 11 lpm, greater than approximately 12 lpm, greater than approximately 13 lpm, greater than approximately 14 lpm, greater than approximately 15 lpm, greater than approximately 16 lpm, greater than approximately 17 lpm, greater than approximately 18 lpm, greater than approximately 19 lpm, and ranges therein, such as approximately 7 lpm to approximately 19 lpm, approximately 8 lpm to approximately 18 lpm, etc. Higher or lower flowrates may also be used. Note that these are average flowrates that are either continuous at a set level or average out to these ranges. Peak flowrates may be higher than the average flowrates. One such mode may be a rapid gas conversion mode, which may be achieved by adding heat to the heat exchanger 801 via a heater 120. Another such mode may bypass the insulation surrounding LOX storage device 703 to preheat the oxygen gas temperature entering the LOX liquid to gas conversion device 705 and effectively increase the surface area of the heat exchanger 801 by including additional surface area of the LOX storage device 703 in the heat exchange. Another such mode may utilize a Stirling engine to utilize the heat across the heat exchanger to power a fan to blow ambient air across the heat exchanger to increase its capacity. Additional details of the Stirling engine are described below.

Ventilator flowrates may demand change during the patients' breathing cycles. Higher flow rates may typically be required during inspiration, and lower or no flowrates may typically be required during exhalation. When interfacing the LOX system to a ventilator, peak flowrates greater than the approximately 6-20 lpm range may be achieved during inspiration by using oxygen gas stored in the oxygen gas storage device 707. The oxygen gas storage device 707 may be recharged during exhalation by the LOX liquid to gas conversion module 705.

The multi-modality of the LOX system 701 may provide for switching based on flow capacity and/or output gas pressure. The mode of operation may be switched manually, automatically, and/or based on input from one or more sensors, such as respiration sensors.

Figure 9:
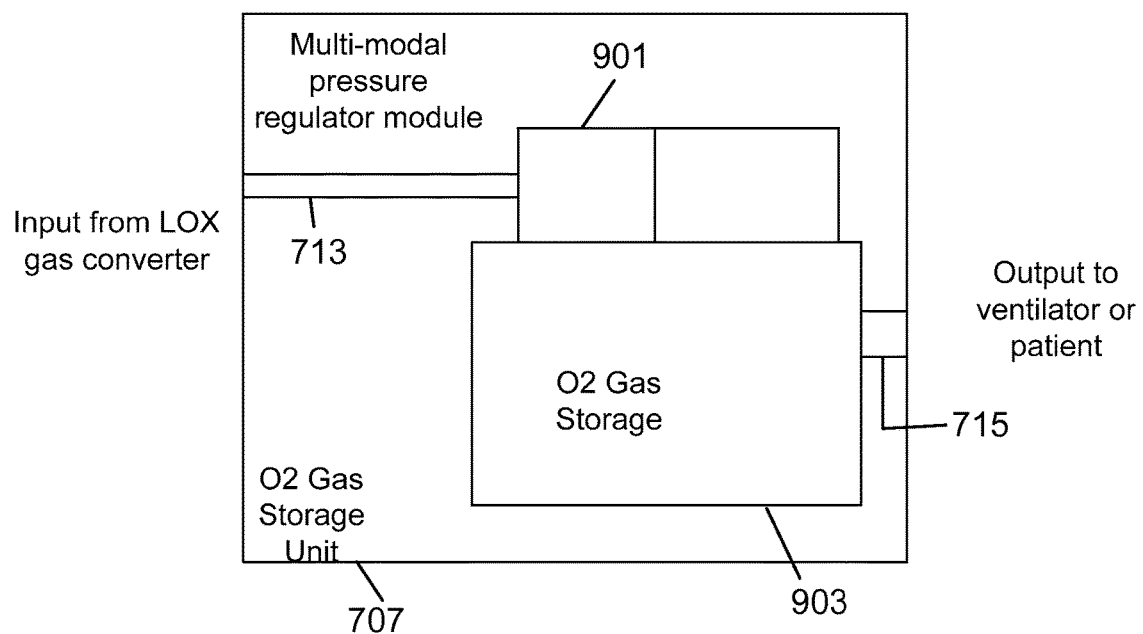
FIG. 9 is a schematic of an oxygen gas storage module, according to an exemplary embodiment.

FIG. 9 shows the oxygen gas storage device 707 according to one embodiment. The oxygen gas storage device 707 may include a multi-modal pressure regulator module 901, for instance to change output pressure between approximately 23 psi when in conserving/airplane mode and approximately 50 psi when in the mode of maximizing patient ventilation. The multi-modal pressure regulator module 901 may typically receive oxygen gas from the LOX liquid to gas conversion device 705 and be in fluid communication with the oxygen gas storage 903, thereby regulating the gas pressure of the oxygen gas storage 903. The multi-modal pressure regulator module 901 may contain multiple pressure regulators that are switched on and off to control the pressure settings. Alternately, the multi-modal pressure regulator module 901 may also contain a singular pressure regulator that is switched between multiple pressure settings, such as by changing a spring force on a regulating diaphragm within the regulator.

The LOX device 701 may have a dual mode operation controlled by the one or more controls 709. The one or more controls 709 may be in communication with the LOX liquid to gas conversion device 705, the oxygen gas storage device 707, and/or other components of the LOX device 701, ventilator, etc. As possible examples, the controls may be affect a heater 120 on the heat exchanger 801, may affect the insulation level surrounding the LOX storage device 703, may switch between multiple pressure regulators within the multi-modal pressure regulator module 901, or may affect the pressure regulator setting within the multi-modal pressure regulator module 901. The one or more controls 709 may include one or more processors and one or more memories.

A first mode of operation for the LOX device 701 may be used for oxygen therapy, while a second mode of operation for the LOX device 701 may be used for powering a ventilator. When in oxygen therapy mode, the conversion rate of liquid to gas may be an average gas flow rate of approximately 1-6 lpm. When in ventilator mode, the conversion rate of liquid to gas may be an average gas flow rate of approximately 4-10 lpm. Having both modes in one device may allow a patient to own only one LOX system, rather than requiring two, one for oxygen therapy and a separate one for mechanical ventilation. When the patient only requires oxygen therapy, the LOX device may only produce an average gas flow rate of approximately 1-6 lpm, and the device does not waste any excess oxygen. When the patient requires mechanical ventilation, the LOX device may produce an average gas flow rate of approximately 4-10 lpm, which may be necessary to obtain sufficient mechanical support. The LOX device may have the ability to automatically determine whether it is being used for oxygen therapy or ventilation therapy and can automatically switch between these modes. For example, the type of patient circuit attached to the LOX device may signal the LOX device whether it is an oxygen therapy tube or a ventilation therapy tube, and the LOX device may switch operating modes accordingly. Alternatively, the ventilator can send a signal to the LOX device that the ventilator is being used for ventilation therapy and the LOX device change accordingly. Alternatively, the LOX device may receive input directly from patient sensors regarding whether the patient requires oxygen therapy or mechanical ventilation. Other signaling systems may be also be used depending on particular situations.

To change from the low conversion rate mode to the high conversion rate mode, the LOX device heat exchanger 801 may be switched from a first state to a second state. For example, liquid oxygen may be channeled through an additional heat exchanger 803 by opening a valve 805, or the heat exchanger 801 may be modified for example by applying heat to the outside of the heat exchanger 801, such as application of a heater 120. The heater may be controlled electrically or by other means.

While the foregoing describes changing the LOX device 701 from one output to a second output, or the heat exchanger 801 having a first and second state, the outputs and states can be more than two, or can be a continuum. For example, the LOX device 701 may adjust the conversion rate automatically within a range based on the needs of the therapy. As such, if the patient is walking briskly while using the ventilation therapy, the LOX device 701 may be signaled by a sensor and/or control system to increase the gas conversion rate to handle the demand of the patient. Conversely, if the LOX device 701 is being used for oxygen therapy and the patient is resting or asleep, the LOX device 701 may be signaled by a sensor and/or control system to reduce the conversion rate to conserve the liquid oxygen supply and prevent wasting converted gas as it is vented to atmosphere.

In an alternative embodiment, a LOX device 701 may have gas produced by the liquid oxygen not vented to atmosphere, but instead collected in another reservoir or cylinder. In this manner, there may be no or minimal waste of the liquid oxygen.

The LOX device 701 may include additional features. The LOX device 701 may include one or more fittings for a high pressure quick connect to attach a ventilator input hose. The output gas may be warmed so as to be more comfortable to the patient when the ventilation gas enters the patient's body. Additionally, moisture or water can be fed into the gas phase of the LOX device 701. Condensation created by the LOX device 701 can be collected, recycled and/or used to moisten the oxygen gas being delivered to the patient. The LOX storage 703 can be a high pressure bladder so that the form factor can be flatter and more convenient for wearing by the patient. The LOX device 701 and ventilator can be integrated or can be modularly attached. The heat exchanger 801 can be black or other colors to modify heat transfer characteristics. The heat exchanger 801 can include fins and/or be made of multiple small tubes to increase surface area. The heat exchanger 801 can also be a tube inside a tube, with a heated annular space and liquid within the inside tube.

Figure 10:
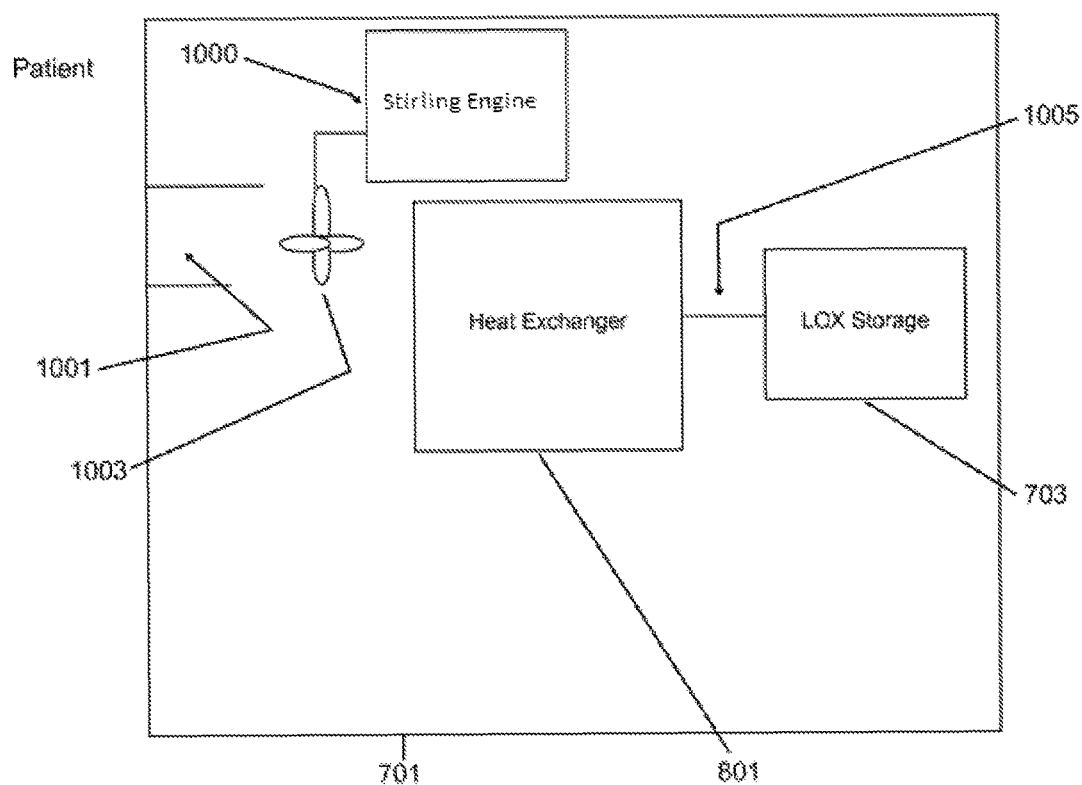
FIG. 10 is a schematic of a Stirling engine, according to an exemplary embodiment.

As shown in FIG. 10, the LOX device 701 can also produce an effect similar to a Stirling engine. The LOX Stirling engine 1000 may be powered by the use of two temperature sinks, one relatively hot 1001 and the other relatively cold 1005. The LOX Stirling engine 1000 may drive a fan 1003 to blow air across the evaporative coils of the LOX system to increase the rate of evaporation. The heat source of the Stirling engine 1000 may be ambient temperature, and the heat sink may be provided by evaporative tubing nearest the LOX storage 703 and/or the area proximal to the LOX storage 703. Once the evaporation process begins, i.e., oxygen begins flowing, the coil may reduce in temperature starting a Stirling engine fan. Once the fan starts, evaporation may become more efficient, i.e., greater convection across tubing may lead to more heat for evaporation. No electrical power may be needed to run this system.

The LOX device output may be of higher pressure and higher flow rate than standard LOX devices to meet the needs of a critical care jet ventilator. The output pressure may typically be approximately 15-80 psi during ventilation mode, and preferably approximately 25-40 psi. A flow rate may typically be approximately 4-20 lpm during ventilation mode, and preferably approximately 8-10 lpm.

While the foregoing descriptions describe the LOX device being used for an ambulatory ventilation therapy, the same principles of the invention can be employed for stationary ventilation. For example, a stationary LOX system can be modified with the embodiments of the invention to be used to power a mechanical ventilator.

Optionally, high frequency low volume ventilation can be delivered by the ventilator and patient interface where very low volumes of gas are delivered at very fast frequencies, such as approximately 5-50 ml at approximately 12-120 cycles per minute, or preferably approximately 10-20 ml at approximately 30-60 cycles per minute. In this manner, substantial minute volumes can be delivered to the lung while controlling the pressures achieved in the airway and lung more closely to a desired level, albeit in an open airway system. This delivery waveform can be continuous or can be synchronized with an inspiratory phase of breathing. Again, different waveforms described can be combined in whole or in part, for example, volumes can be synchronized and delivered in one shot during inspiration, and then high frequency low volume ventilation can be delivered during exhalation. It should also be noted that ventilation gas delivery, when activated, can gradually ramp up so that it is not a sudden increase in amplitude, which could arouse the patient.

While the foregoing has described the therapy of this invention using a nasal interface, other interfaces may also be included in the invention such as a trans-oral interface. The tip of a catheter can be proximal to the mouth entrance, coplanar with the mouth entrance, or recessed inside the mouth between the lips and the jaw line. The catheter can be shaped to be routed along the teeth, either on the buccal side or lingual side of the teeth, or through the center of the mouth. The catheter can be positioned so that a portion of the catheter rests on the superior surface of the tongue, or can be positioned so that a portion of the catheter rests against the inferior surface of the hard palate, in which case the distal tip of the catheter may be angled or curved inferiorly away from the palate and towards the oropharyngeal airway. The catheter can be bifurcated so that there is a left and right catheter positioned on both the right and left side of the mouth. The catheter can be integral to a bite block or mouth guard. The catheter preferably is easily inserted and removed from the patient's mouth. All of the appropriate details described previously in conjunction with the nasal interface may apply to the oral catheter used in embodiments of the invention.

The present invention can also be used with an endotracheal tube (ET) interface. This version of the interface can be helpful to institutions that walk their patients during the weaning stages off of invasive mechanical ventilation. Walking patients that are on ICU ventilators is typically very onerous because the patient must have the assistance of a number of medical staff to move the large and complex ICU ventilator alongside the patient. The present invention may be used to help a patient walk, while receiving adequate ventilatory support from the ventilation system and interface described in this invention. In this embodiment, the ET tube connector may include an attachment for the ventilation interface of this invention. The patient can breathe ambient air spontaneously through the proximal end of the ET tube proximal connector, which is left open, while the patient's spontaneous breaths are efficaciously augmented by the ventilation system and catheter interface of the invention. Optionally, if it is desired to apply positive end-expiratory pressure (PEEP), a special PEEP valve may be included for attachment to the end of the ET tube. The special PEEP valve may include a one way valve so that ambient air may be easily entrained into the ET tube toward the patient's lung by a jet nozzle of the invention, but also allows exhalation through the PEEP valve, while maintaining the desired PEEP level. Preferably, the patient can still also breathe room air spontaneously through the PEEP valve through an inspiratory valve integral to or in parallel with the PEEP valve. The ventilator used in the present invention can provide PEEP as previously described by delivering gas with the appropriate waveform during the patient's expiratory phase. The catheter tip can be slightly proximal to the proximal end opening of the ET tube proximal connector, or can be coplanar with the proximal end opening, or can be inserted into the ET tube to the appropriate depth, typically at around the mid-point, but the appropriate depth may depend on other variables of the system. The depth can be adjustable to optimize the entrainment and performance or function for individual situations, as required clinically or for patient tolerance. The ET tube connector used in this embodiment of the invention may provide the necessary jet pump geometry as previously described in conjunction with the nasal cannula outer concentric tube. The ET tube connector can include a jet inlet, jet throat and diffuser section. Or, alternatively, the ET tube can be of a special configuration, which incorporates dimensions and geometries advantageous to the jet pump performance. All of the appropriate details described previously with the nasal interface, apply to the ET tube catheter interface used in this version of the invention. In addition, PEEP can be included in the other patient interfaces described in the invention by including a similar special PEEP valve for each of the different patient interfaces.

As previously indicated, FIG. 1 is a block diagram describing an embodiment of the invention with expanded features and capabilities. A ventilator module includes or is in communication with several other accessories or functional modules.

A transmitter and/or receiver 103 may be included to transmit and/or receive information regarding the patient, the patient's therapy, and the ventilator performance to a remote location for review, analysis and archival. For example, the patient's compliance to the therapy or utilization of the therapy can be monitored and assessed. Important information can be trended, for example the patient's breath rate, I:E ratio or depth of breathing. Also, information can be sent to the ventilator, for example programming of settings to titrate the ventilator output to meet the needs of the patient.

An internal or external humidifier 105 can be included for extended uses of the therapy, or if using in dry climates. The humidity can be delivered using a humidification generator that is integral or coupled with the ventilator, or using a stand alone humidifier. The humidified air or oxygen can be delivered through the gas delivery channel of the gas delivery circuit, or through another lumen in the gas delivery circuit as previously described, or through a separate cannula or tubing. For extended use, when the patient is likely to be stationary, the humidification system can be a stationary system and capable of delivering a relative high amount of humidity, and for periods of mobility, the patient can either not receive humidification, or use a portable humidification system that is capable of delivering relatively a small amount of humidity, due to size and energy consumption constraints.

In addition to a LOX system 107, a compressed air source 109 can be included, typically external attached to the ventilator, however optionally internal to the ventilator if the therapy is being used for stationary use, for example in the home. Examples of a compressed air source 109 may include a pressurized air source and/or a generator. A blender 111 can be included to control the fractional delivered oxygen in a gas delivery circuit 113. The blender 111 may receive input from the compressed air source 109 and/or the LOX system 107 and output to a ventilator 115. The blender 111 may be used to titrate the amount of oxygen needed, either based on a clinical determination, or by pulse oximetry or other biofeedback signals. For oxygen concentrations needed that are less than 100%, the system can use compressed air from a compressor, tank or wall source, or the air can be entrained into the system from the pressurized oxygen gas, for example at the patient interface, or elsewhere in the system, such as the gas delivery circuit or ventilator. If air is entrained in, it can be entrained in from room air. For treating other diseases and applications, other therapeutic gases can also be delivered by blending into the delivered gas, such as helium-oxygen mixtures, nitric oxide, or combinations of air, oxygen, helium and nitric oxide. A pulse oximeter 117 can be used to determine correct blender settings to achieve proper oxygen saturation. The pulse oximeter 117 can also be used to titrate other settings of the ventilator system to meet the physiological needs of the patient, or to control the rapid gas conversion mode of a LOX system used with a nasal cannula instead of a ventilator. A controller may use a signal from one or more pulse oximeters to switch modes of the LOX system. In addition to compressed supplies of oxygen and air gas, the ventilator can include internal or external air and oxygen generating means, such as a pump or blower to create pressurized air, and an oxygen generator and/or pump to create pressurized oxygen gas. The oxygen source can also be liquid oxygen, or a liquid oxygen generating system.

Because the therapy is frequently used to help activities of daily living, and to promote activity, a pedometer 119 and/or actigraphy sensor 121 can be included internal to or external to the ventilator system. A carbon dioxide monitor 131 may also be included.

An external respiration sensor 123 can be included, such as a respiratory muscle effort sensor, a chest impedance sensor, or other types of respiration, such as a tracheal microphone or vibration sensor. The external sensor 123 may be used either as a redundant sensor to a nasal airflow or nasal pressure sensor 125, or to complement the information obtained from the nasal airflow sensor, or in place of the nasal airflow sensor. The nasal airflow or nasal pressure sensor 125 may measure spontaneous respiration. The nasal airflow or nasal pressure sensor may be located at a non-invasive open nasal ventilation interface 129 or at other appropriate locations.

A drug delivery module 127 can be incorporated internally or externally to the ventilator system. Due to challenges with current aerosolized drug delivery inhalers, the current invention can be used to propel and deposit medication particles deep in the respiratory system, without a carrier propellant. Because a patient's using the therapy often also requires prescription medication, this may be a convenient and efficient way to administer the medication.

When the therapy is being used for respiratory support, the user may have two options; (1) wearing or toting the ventilator so that the user can be ambulatory or enjoy the activities of daily living, or (2) stationary use, in the event the patient plans on being stationary or does not have the ability to ambulate. The delivery circuit can optionally be provided in a 25-100 foot length, such that the gas source and ventilator can be stationary in the patient's home, while the patient can move around their home while wearing the interface and receiving the therapy. Or, the gas source can be stationary, and connected to the ventilator with a 25-100 foot hose, so that the patient can wear or tote the ventilator and be mobile within the range of the hose. In certain embodiments, the gas delivery circuit may be connected to a blender, which receives pressurized oxygen and pressurized air from, for example, the hospital pressurized gas supply. In these applications, in which mobility may be less important, the system can be attached to the house gas supply, and higher levels of therapy can be delivered, as well as PEEP therapy during exhalation. All of these different options of stationary use and mobile use apply to the various different interface techniques described in the foregoing.

The ventilator can be self-contained with a battery and gas supply to enable it to be borne by the patient, so that the patient can ambulate and participate in activities of daily living, which is made possible by the respiratory support they are receiving from the ventilator, but in a package that can easily be borne.

For the therapy described in this invention to be more effectively titrated to the needs of the patient, the ventilator system can perform a determination to determine the level of respiratory support needed. To accomplish this, the ventilator can titrate the output to the needs of the patient, for example, during ambulation or activity the output can increase. Alternatively, during higher respiratory rates as measured by the spontaneous breath sensor, the output can increase. Or during higher breath effort as measured by the breath sensor, the output can increase. Other biofeedback signals can be used. In addition to the output increasing or changing to meet the respiratory needs of the patient, the timing of the ventilator output relative to the patient's spontaneous inspiratory phase, and the output waveform can change to meet the comfort and physiological needs of the patient. For example, during exercise, the output can change from an early delivery at 75 ml with an ascending waveform, to being triggered with a delay to start for example 100 msec after the start of inspiration, and with a decelerating waveform.

To facilitate integration of this new therapy into the existing therapeutic paradigms, a convertible system may be provided. Specifically, the patient interface can be modular, such that a patient can be administered conventional oxygen therapy with a typical or slightly modified oxygen nasal cannula. Then, when it is desired to switch the patient to this new therapy, an additional component, such as an outer concentric tube, may be added to the nasal cannula to create the jet pump design and to position the distal tips of the cannula properly to achieve the function of this invention. Alternatively, for example, a switch on the gas delivery equipment can be switched to change the output of the equipment from oxygen therapy, to this therapy, by for example, enabling additional breath sensing functions, timing functions, waveform functions, and switching to the output amplitude necessary. The LOX portions of the system can be modular as well, for example, they can be replaced with oxygen gas cylinders, wall oxygen, compressed gas, and an oxygen-air blender.

It should be noted that the different embodiments described above can be combined in a variety of ways to deliver a unique therapy to a patient and while the invention has been described in detail with reference to the preferred embodiments thereof, it will be apparent to one skilled in the art that various changes and combinations can be made without departing for the present invention. Also, while the invention has been described as a means for mobile respiratory support for a patient, it can be appreciated that still within the scope of this invention, the embodiments can be appropriately scaled such that the therapy can provide higher levels of support for more seriously impaired and perhaps non-ambulatory patients or can provide complete or almost complete ventilatory support for non-breathing or critically compromised patients, or can provide support in an emergency, field or transport situation. Also, while the invention has mostly been described as being administered via a nasal interface it should be noted that the ventilation parameters can be administered with a variety of other airway interface devices such as ET tubes, tracheostomy tubes, laryngectomy tubes, cricothyrotomy tubes, endobronchial catheters, laryngeal mask airways, oropharyngeal airways, nasal masks, trans-oral cannula, nasal-gastric tubes, full face masks, etc. And while the ventilation parameters disclosed in the embodiments have been mostly specified to be compatible with adult respiratory augmentation, it should be noted that with the proper scaling the therapy can be applied to pediatric and neonatal patients. Further, while the target disease states have mostly been described as respiratory insufficiency and sleep apnea, other breathing, lung and airway disorders can be treated by the therapy with the requisite adjustment in ventilation parameters, for example, ALS, neuromuscular disease, spinal cord injury, influenza, CF, ARDS, lung transplant bridging, and other diseases can be addressed with this therapy, as well as mass casualty, pandemic, military, bridge and transport applications. Lastly, while the invention has been described as a stand alone therapy, the therapy can be modular, for example a ventilation system can be adapted which can switch between invasive or non-invasive or other closed system ventilation modes and the non-invasive open ventilation mode described herein. Or, the therapy can be used simultaneously in conjunction with other modes of ventilation, such as during a conscious sedation medical procedure in which the patient is ventilated with a conventional ventilator as a back up means of respiration while the patient receives ventilation from the mode described herein.

Although the foregoing description is directed to the preferred embodiments of the invention, it is noted that other variations and modifications will be apparent to those skilled in the art, and may be made departing from the spirit or scope of the invention. Moreover, features described in connection with one embodiment of the invention may be used in conjunction with other embodiments, even if not explicitly stated above. The present invention may be embodied in other specific forms without departing from its spirit or essential characteristics. The described embodiments are to be considered in all respects only as illustrative and not restrictive.

The invention claimed is:

1. A portable liquid oxygen system providing an average flow rate of oxygen gas at approximately 6 lpm to approximately 20 lpm using a rapid gas conversion mode, the portable liquid oxygen system comprising:
   a liquid oxygen store;
   a heat exchanger for evaporating liquid oxygen from the liquid oxygen store into oxygen gas;
   a Stirling engine having a heat source and a heat sink, wherein the heat source is an opening to ambient air and wherein the heat sink is proximal to the liquid oxygen store; and
   a fan, wherein during the rapid gas conversion mode, the Stirling engine drives the fan to blow ambient air from the heat source across the heat exchanger to more rapidly evaporate liquid oxygen from the liquid oxygen store into oxygen gas.

2. The portable liquid oxygen system of claim 1, wherein the portable liquid oxygen system weighs less than 10 pounds.

3. The portable liquid oxygen system of claim 1, wherein the heat sink is in thermal communication with the liquid oxygen store.

4. The portable liquid oxygen system of claim 1, further comprising one or more respiration sensors, wherein the rapid gas conversion mode is activated based upon signals received from the one or more respiration sensors.

5. The portable liquid oxygen system of claim 1, further comprising one or more pulse oximeters, wherein the rapid gas conversion mode is activated based upon signals received from the one or more pulse oximeters.

6. A ventilation system comprising:
   a portable ventilator; and
   a portable liquid oxygen (LOX) system providing a flow rate of oxygen gas evaporated from a liquid oxygen store to the portable ventilator at approximately 6 lpm to approximately 20 lpm using a rapid gas conversion mode, the portable LOX system comprising:
      a heat exchanger for evaporating the liquid oxygen from the liquid oxygen store into oxygen gas;
      a Stirling engine having a heat source and a heat sink, wherein the heat source is an opening to ambient air and wherein the heat sink is proximal to the liquid oxygen store; and
      a fan, wherein during the rapid gas conversion mode, the Stirling engine drives the fan to blow ambient air from the heat source across the heat exchanger to more rapidly evaporate liquid oxygen from the liquid oxygen store into oxygen gas.

7. The ventilation system of claim 6, wherein the portable ventilator and the portable liquid oxygen system are integrated into a single portable or wearable unit.

8. The ventilation system of claim 6, wherein the portable liquid oxygen system weighs less than 10 pounds.

9. The ventilation system of claim 6, further comprising a patient interface, wherein the patient interface is a nasal interface, a mask, an endotracheal tube, a tracheostomy tube, or a transoral tube.

10. The ventilation system of claim 6, wherein the ventilator is wearable.

11. The ventilation system of claim 6, further comprising a blender for titrating an amount of oxygen gas output to the ventilator.

12. The ventilation system of claim 6, wherein the heat sink is in thermal communication with the liquid oxygen store.

13. The ventilation system of claim 6, further comprising one or more respiration sensors, wherein the rapid gas conversion mode is activated based upon signals received from the one or more respiration sensors.

14. The ventilation system of claim 6, further comprising one or more pulse oximeters, wherein the rapid gas conversion mode is activated based upon signals received from the one or more pulse oximeters.

15. A liquid oxygen system having a rapid gas conversion mode, the liquid oxygen system comprising:
 a liquid oxygen store;
 a heat exchanger for evaporating liquid oxygen from the liquid oxygen store into oxygen gas;
 a Stirling engine having a heat source and a heat sink, wherein the heat source is an opening to ambient air and wherein the heat sink is proximal to the liquid oxygen store; and
 a fan, wherein during the rapid gas conversion mode, the Stirling engine drives the fan to blow ambient air from the heat source across the heat exchanger to more rapidly evaporate liquid oxygen from the liquid oxygen store into oxygen gas.

16. The liquid oxygen system of claim 15, wherein the liquid oxygen system is portable.

17. The liquid oxygen system of claim 15, wherein the heat sink is in thermal communication with the liquid oxygen store.

18. The liquid oxygen system of claim 15, further comprising one or more respiration sensors, wherein the rapid gas conversion mode is activated based upon signals received from the one or more respiration sensors.

19. The liquid oxygen system of claim 15, further comprising one or more pulse oximeters, wherein the rapid gas conversion mode is activated based upon signals received from the one or more pulse oximeters.

* * * * *